US008637090B2

(12) United States Patent
Ohtake et al.

(10) Patent No.: US 8,637,090 B2
(45) Date of Patent: Jan. 28, 2014

(54) GALLIUM FORMULATION FOR THE TREATMENT AND PREVENTION OF INFECTIOUS DISEASES

(75) Inventors: Satoshi Ohtake, Milpitas, CA (US); Vu Truong-Le, Campbell, CA (US); David Lechuga-Ballesteros, San Jose, CA (US); Luisa Yee, Los Altos, CA (US); Binh V Pham, Mountain View, CA (US); Russell Martin, Los Gatos, CA (US); Atul Saxena, Milpitas, CA (US)

(73) Assignee: Aridis Pharmaceuticals, San Jose, CA (US)

( * ) Notice: Subject to any disclaimer, the term of this patent is extended or adjusted under 35 U.S.C. 154(b) by 0 days.

(21) Appl. No.: 13/318,774

(22) PCT Filed: May 4, 2010

(86) PCT No.: PCT/US2010/033599
§ 371 (c)(1),
(2), (4) Date: Feb. 29, 2012

(87) PCT Pub. No.: WO2011/005354
PCT Pub. Date: Jan. 13, 2011

(65) Prior Publication Data
US 2012/0148635 A1 Jun. 14, 2012

Related U.S. Application Data

(60) Provisional application No. 61/175,457, filed on May 4, 2009.

(51) Int. Cl.
*A61K 33/24* (2006.01)

(52) U.S. Cl.
USPC .......................................... 424/650; 514/492

(58) Field of Classification Search
None
See application file for complete search history.

(56) References Cited

U.S. PATENT DOCUMENTS

| 5,700,487 A * | 12/1997 | Gerber et al. ............. 424/650 |
| 6,203,822 B1 | 3/2001 | Schlesinger et al. |
| 7,482,024 B2 * | 1/2009 | Kuo et al. ............. 424/499 |
| 2008/0241275 A1 * | 10/2008 | Perl et al. ............. 424/650 |
| 2009/0275655 A1 | 11/2009 | Warrell, Jr. et al. |

FOREIGN PATENT DOCUMENTS

| WO | WO 97/32592 A1 | 9/1997 |
| WO | WO 03/053347 A2 | 7/2003 |
| WO | WO 2007/087461 * | 8/2007 |
| WO | WO 2007/087461 A2 | 8/2007 |

OTHER PUBLICATIONS

Padian et al., Title: Biometical INterventions to prevent HIV infection: evidence, challenges and way forward; Lancet, 2008, vol. 372, pp. 585-599.*
Hayes et al.; Title: Bone Scanning with Gallium-68: a carrier Effect; J. Nuclear Med., vol. 6, pp. 605-610; published 1965.*
Bernstein et al.; "Mechanisms of therapeutic activity for gallium"; Pharmacol. Rev.; 50(4):665-682 (Dec. 1998).
Kaneko et al.; "The transition metal gallium disrupts *Pseudomonas aeruginosa* iron metabolism and has antimicrobial and antibiofilm activity"; *J. Clin. Invest.*; 117(4):877-888 (Apr. 2007).
Supplementary European Search Report from EP 10797479.2, mailed Nov. 2, 2012 (9 pages).
Clausén, et al., "Spectroscopic studies of aqueous gallium(III) and aluminum(III) citrate complexes," J. Inorg Biochem., vol. 99(3), pp. 716-726 (Mar. 2005).
Deleon, et al., "Gallium Maltolate Treatment Eradicates *Pseudomonas aeruginosa* Infection in Thermally Injured Mice," Antimicrob Agents Chemother., vol. 53(4), pp. 1331-1337 (Apr. 2009)
Sung, et al., "Dry Powder Nitroimidazopyran Antibiotic PA-824 Aerosol for Inhalation," Antimicrob Agents Chemother., vol. 53(4), pp. 1338-1343 (Apr. 2009).
International Search Report and Written Opinion for PCT/US2010/033599, dated Jan. 3, 2011.
Adamson (1975) Studies on the antitumor activity of gallium nitrate (NSC-15200) and other group lila metal salts in Cancer Chemother. Rep. 59:599-610.
Amano (2006) Pulmonary infections in patients with rheumatoid arthritis who have received anti-TNF therapy in Intern. Med. 45:991-992.
Apseloff, G.; "Therapeutic Uses of Gallium Nitrate: Past, Present and Future"; Am. J. Therapeutics; 6:327-339 (1999).
Brain (1980) Macrophage damage in relation to the pathogenesis of lung diseases in Environ. Health Perspectives 35:21-28.
Chang et al.; "Carbon-13 Fourier Transform Nuclear Magnetic Resonance Study of Gallium Citrate in Aqueous Solution"; *J. Am. Chem. Soc.*; 99(18):585-5863 (1977).
Chitambar (1997) Evaluation of continuous-infusion gallium nitrate and hydroxyurea in combination for the treatmen of refractory non-Hodgkin's lymphoma in Am. J. Clin. Oncol. 20:173-178.

(Continued)

*Primary Examiner* — Richard Schnizer
*Assistant Examiner* — Yanzhi Zhang
(74) *Attorney, Agent, or Firm* — Kilpatrick Townsend & Stockton LLP

(57) ABSTRACT

A method and composition for treatment of bacterial infections caused by gram negative or gram positive bacteria such as *Staphylococcus aureus, Rhodococcus equi, Mycobacterium tuberculosis, Escherichia coli, Klebsiella pneumoniae, Klebsiella oxytoca, Pseudomonas aeruginosa, Haemophilus influenzae, Proteus mirabilis, Enterobacter* species, *Serratia marcescens* as well as those caused by *Burkholderia cepacia, Stenotrophomonas maltophilia, Alcaligenes xylosoxidans,* and multidrug resistant *Pseudomonas aeruginosa*, using a formulation containing gallium (III), in a pharmaceutically acceptable salt or complex thereof.

13 Claims, 14 Drawing Sheets

(56) References Cited

OTHER PUBLICATIONS

Cowley (1997) Airway surface fluid composition in the rat determined by capillary electrophoresis in Am. J. Physiol., 273:L895-L899.
Duddu (2002) Improved lung delivery from a passive dry powder inhaler using an engineered PulmoSphere powder in Pharmaceutical Research 19:689-695.
Duncan (2005) Transplant-related immunosuppression: a review of immunosuppression and pulmonary infections in Proc. Am. Thorac. Soc. 2:449-455.
Edwards (2002) Bioengineering of therapeutic aerosols in Annu. Rev. Biomed. Eng. 4:93-107.
Fick (1989) Pathogenesis of the pseudomonas lung lesion in cystic fibrosis in Chest 96:158-164.
Foster (1986) Gallium nitrate: the second metal with clinical activity in Cancer Treat Rep 70:1311-1319.
Geller (2007) Novel tobramycin inhalation powder in cystic fibrosis subjects: pharmacokinetics and safety in Pediatr. Pulmonol. 42:307-313.
Genta (2003) Ganite package insert (4 pages).
Gray (2008) Sputum proteomics in inflammatory and suppurative respiratory diseases in Am. J. Respir. Cril. Care Med. 178:444-452.
Griese (2004) Pulmonary surfactant, lung function, and endobronchial inflammation in cystic fibrosis in Am. J. Respir. Cril. Care Med. 170:1000-1005.
Hawe (2006) Physico-chemical lyophilization behavior of mannitol, human serum albumin formulations in Eur J Pharm Sci. 28:224-232.
Hawkes et al.; "Solid and Solution State NMR Spectra and the Structure of the Gallium Citrate Complex $(NH_4)_3[Ga(C_6H_5O_7)_2] \cdot 4H_2O$"; *Eur. J. Inorg. Chem.*; pp. 1005-1011 (2001).
Herlant-Peers (1981) Structures of fifteen oligosaccharides isolated from new-born meconium in Eur J Biochem. 117:291-300.
Lange (2009) Chronic obstructive pulmonary disease and risk of infection in Pneumonol Alergol Pol. 77(3):284-288.
Lechuga-Ballesteros (2008) Trileucine improves aerosol performance and stability of spray-dried powders for inhalation in J. Pharm. Sci. 97:287-302.
Marshall (2009) Citrate-mediated iron uptake in *Pseudomonas aeruginosa*: involvement of the citrate-inducible FecA receptor and the FeoB ferrous iron transporter in Microbiology 155:305-315.
Matzapetakis et al.; "Synthesis, pH-Dependent Structural Characterization, and Solution Behavior of Aqueous Aluminum and Gallium Citrate Complexes"; *Inorg. Chem.*: 40:1734-1744 (2001).
Mokra (2007) Aminophylline treatment in meconium-induced acute lung injury in a rabbit model in J. Physiol. Pharmacol. 58:Suppl. 5:399-407.
Moody (1985) Iron transport and its relation to heme biosynthesis in *Rhodopseudomonas sphaeroides* in J. Bacteriol. 161:1074-1079.
Nielson (1986) Electrolyte composition of pulmonary alveolar subphase in anesthetized rabbits in J. Appl. Physiol. 60:972-979.
Normandin (1990) Sampling of lung interstitial fluid in intact dog in J. Surg. Res. 48:91-98.
Plasencia (2007) Influence of high mutation rates on the mechanisms and dynamics of in vitro and in vivo resistance development to single or combined antipseudomonal agents in Antimicrobial Agents Chemotherapy 51:2574-2581.
Poole (2009) Intranasal organic dust exposure-induced airway adaptation response marked by persistent lung inflammation and pathology in mice in Am. J. Physiol. Lung Cell. Mol. Physiol. 296:L1085-1095.
Rogers (1994) Airway goblet cells: responsive and adaptable front-line defenders in Eur. Respir. J. 7:1690-1706.
Takemura (2003) Effect of immunoglobulin G from cows immunized with ferric citrate receptor (FecA) on iron uptake by *Escherichia coli* in J. Dairy Sci. 86:133-137.
Vreim (1976) Protein composition of lung fluids in acute alloxan edema in dogs in Am. J. Physiol. 230:376-379.
West (2002) Respiratory infections with *Pseudomonas aeruginosa* in children with cystic fibrosis: early detection by serology and assessment of risk factors in J. Am. Med. Assoc. 287:2958-2967.
White (2005) Exubera: pharmaceutical development of a novel product for pulmonary delivery of insulin in Diabetes Technology & Therapeutics 7:896-906.

\* cited by examiner

Figure 2

GALLIUM FORMULATION FOR THE TREATMENT AND PREVENTION OF INFECTIOUS DISEASES

PRIORITY

This application is the U.S. National Stage entry under §371 of International Application No. PCT/US2010/033599, filed May 4, 2010, which claims priority from U.S. Provisional 61/175,457, filed May 4, 2009. The International Application and U.S. provisional application are each incorporated herein by reference.

STATEMENT CONCERNING FEDERALLY SPONSORED RESEARCH OR DEVELOPMENT

Certain aspects of the invention disclosed herein were made with United States government support under NIH R41AI072866-01. The United States government may have certain rights in the invention.

FIELD OF THE INVENTION

The invention encompasses a method to formulate gallium for use as an anti-infective for treatment of gram-negative and gram-positive bacteria, viruses, fungi, and protozoa. In particular, the methods describe liquid and dry powder formulations containing gallium in a pharmaceutically acceptable salt or complex thereof, delivered as a liquid or dry powder aerosol.

BACKGROUND OF THE INVENTION

Approximately 100 antibiotics are in use today, 15 in phase 2 or 3 clinical studies, 13 of which are against multi drug-resistant gram-positive and 2 against extended spectrum β-lactamase producing gram-negative bacteria. Heavy antibiotic use and communal spread of bacteria have greatly increased antibiotic resistance, and this problem is continually increasing in severity. The bacterium *Pseudomonas aeruginosa* (Pa) is a prime example: 30% of clinical isolates from intensive care unit (ICU) or nursing home patients are now resistant to 3 or more drugs, and a similar situation exists for other organisms. Another reason why conventional antibiotics generally work poorly in chronic infections is that the infecting organisms live in biofilms, which are surface-associated bacterial communities encased in a complex biopolymeric matrix. Physiological changes inherent to biofilm growth make bacteria far more resistant to killing by the immune system and antibiotics than cells in the free-living (planktonic) state. Examples of biofilm infections include the airway infections in cystic fibrosis (CF) patients, chronic wound and sinus infections, endocarditis, and medical device infections, among others.

The prominence of Pa infection and its impact on the lungs of CF patients is well documented (Fick (1989) Chest 96:158-164; Hoiby (1993) Annu Rev. Med. 44:1-10). Existing therapies, such as aminoglycoside antibiotics, eventually have little or no impact on disease progression and ultimately, 80-95% of CF patients succumb to respiratory failure due to chronic Pa infection and airway inflammation. Despite recent advances in disease management, the lungs of CF patients are particularly susceptible to chronic bacterial infections. Moreover, current therapies to control Pa infections in CF patients are inconvenient and with modest impact on mortality. There is a consensus that because Pa resides in the lung at the tissue-air interface, the most effective route of antibiotics drug delivery is locally by direct inhalation. The current standard of care to treat Pa infection in CF patients is twice-daily treatment of tobramycin solution administered by oral inhalation for alternating 28-day on-off cycles. The drug administration involves nebulizer priming, followed by approximately half an hour of inhalation at each dosing. Given that CF patients are increasingly burdened with multiple treatment regimens on an average day, the quality of life has become an important factor in the development of new drug therapies; for example, nearly three hours of the day are spent dealing with inhalation therapy (i.e. saline solution, antibiotic and DNase treatment) (Geller, D. E., et al (2007) Pediatric Pulmonology 42:307-313).

Inhaled tobramycin solution represents a significant advancement in treating pulmonary infection in CF patients. Further improvements have been enabled by recent advances in powder engineering, allowing for additional reduction in dose level as well as dosing time. For example, inhalation of tobramycin dry powder produced serum tobramycin PK profiles comparable to those obtained via nebulization, with a significant reduction in dose and shorter administration time. Four capsules of 28 mg (total tobramycin dose 112 mg) produced comparable systemic exposure to 300 mg inhaled nebulized solution, in less than one-third the administration time (Geller, D. E., et al (2007) Pediatric Pulmonology 42:307-313). In addition, tobramycin dry powder increased the local lung exposure, increasing efficacy, and reduced systemic exposure, thereby reducing systemic side effects. The data demonstrated that recent technological improvements in particle engineering and in inhalation devices have enabled a fast, safe, and efficacious delivery of high payload of powder even to the already susceptible CF patients' lungs. However, despite the delivery advances which achieved higher local tobramycin concentrations and delayed the onset of bacterial resistance development, the occurrence of Pa-resistant strains continues (Plasencia, V., et al (2007) Antimicrobial Agents Chemotherapy 51:2574-2581). Therefore, there is not only a need for new classes of safe and efficacious anti-infective agents, but ones that can be delivered locally to the lung with simple and convenient administration experience.

The effectiveness of gallium against Pa has stimulated interests in developing this drug candidate for CF lung infections. For many years, gallium has been used for the treatment of several human and animal disorders, including hypocalcaemia and osteoporosis (Warell et al., U.S. Pat. No. 4,529,593; Bockman et al., U.S. Pat. No. 4,704,277; Bradley et al., U.S. Pat. No. 5,196,412; Bradley et al., U.S. Pat. No. 5,281,578), cancer (Adamson et al. (1975) Cancer Chemothe. Rept 59:599-610; Foster et al. (1986) Cancer Treat Rep 70:1311-1319; Chitambar et al. (1997) Am. J. Clin. Oncol. 20:173-178), wound healing and tissue repair (Bockman et al., U.S. Pat. No. 5,556,645; Bockman et al., U.S. Pat. No. 6,287,606), as well as both intracellular and extracellular infections (Schlesinger et al., U.S. Pat. No. 5,997,912; Schlesinger et al., U.S. Pat. No. 6,203,822; Bernstein, et al., International Patent Application Publication no. WO 03/053347; Perl, U.S. 2008/0241275). These patent documents, and any U.S. counterparts, are expressly incorporated herein by reference. Gallium was shown to be both bacterial growth inhibiting as well as bactericidal as the minimum inhibitory concentration ($MIC_{90}$) and bactericidal concentration (MBC) of gallium against Pa are both approximately 0.7 µg/mL (Kaneko et al. (2007) J. Clin. Invest. 117:877-888). Gallium nitrate has demonstrated strong bactericidal activity against many gram-negative and gram-positive bacteria. The effectiveness of gallium nitrate against a variety of bacteria found to chronically colonize the lungs of CF patients, such as *Pseudomonas*

*aeruginosa, Burkholderia cepacia*, and methicillin-resistant *Staphylococcus aureus* (MRSA), makes it a promising drug candidate for treatment in CF.

Local delivery is often the most effective method to maximize bioavailability to the target site while minimizing systemic exposure. For local lung delivery to treat lung infections, there is evidence demonstrating that localized delivery of gallium nitrate to the respiratory tract is protective in mouse Pa challenge models (Kaneko et al. (2007) J. Clin. Invest. 117:877-888). In these studies, intratracheal (i.t.) inoculation of a lethal dose of Pa followed by nasal instillation of a bolus of liquid containing gallium nitrate resulted in good protection, even under in vivo Pa biofilm colonization conditions. While nasal instillation of a bolus dose is frequently used in many mouse lung studies, it is known that delivering liquid aerosols through the nasal route resulted in poor (less than 10% of delivered dose) lung penetration, most likely due to inertial impaction of the aerosol droplets onto the tortuous anatomical structures in the nasal cavity (Bryant et al. (1999) Nucl. Med. Commun. 20:171-174). Thus the minimal gallium-protective dose observed for the nasal administration route is likely significantly higher than direct i.t. application or if pulmonary inhalation is used.

The current invention is a high concentration liquid formulation for gallium containing compounds that could be efficiently delivered from conventional nebulizers with short (<10 minutes) dosing times. Optimum formulation for such liquid gallium composition may require a minimum amount of counterion, such as citrate, to buffer against lung fluid to prevent gallium precipitation. Furthermore, the aerosol droplet size may be modulated by incorporating viscosity-enhancing components, such as mannitol, which in addition may be used to adjust the osmolality of the gallium composition. The increased viscosity of the gallium composition may also impact the time required to deliver the necessary dose. Similar effects on droplet size and delivery time may be observed by increasing the ionic strength of the gallium composition. A successful powder formulation for inhalation requires optimal balance among several physicochemical attributes including geometric and aerodynamic particle size, physical and chemical stability as well as aerosol dispersibility. A second key inventive contribution is a room temperature stable inhalable dry powder formulation of gallium with the appropriate aerosol properties for deep lung delivery using commercially available dry powder inhalers (such as Tubohaler™, Cyclohaler™, Turbospinhaler™). The formulations resulted in gallium nitrate dosage forms that are compatible with simple, cost-effective, portable dry powder inhalers that can be conveniently and easily self-administered. Spray drying was used to prepare the gallium nitrate dry powder for inhalation. For inhalable dry powder manufacturing, spray drying is the method of choice as it is the most effective and direct process to manufacture powders with appropriate aerosol properties for deep lung delivery. Its use has been demonstrated with tobramycin dry powder (Duddu, S. P., et al. (2002) Pharmaceutical Research 19:689-695), and with inhaled insulin product Exubera™, the first protein to be delivered through the pulmonary route (White, S., et al. (2005) Diabetes Technology & Therapeutics 7, 896-906). Spray drying is an ideal process to create homogeneous particles containing precise amounts of drug and excipients which can be engineered to perform in a predictable manner with a handheld delivery device. The feasibility of preparing spray dried powders containing antibiotics has been previously demonstrated (Lechuga-Ballesteros, et al. (2008) J. Pharm. Sci. 97:287-302).

SUMMARY OF THE INVENTION

The methods of the present invention include preparing a solution or suspension of gallium for use as an antiinfective. In a preferred embodiment of this invention, a method is disclosed for preparing an aerosol composition, liquid or dry powder, comprising a therapeutically effective dose of gallium in the form of a pharmaceutically acceptable salt or complex, wherein said composition is suitable for delivery to the lung or deep lung by inhalation and comprising from about 1% by weight to about 90% by weight gallium. In a preferred aspect of this embodiment, the salt is a counterion selected from the group consisting of nitrate, citrate, chloride, or a mixture thereof. The complexing agent is selected from the group consisting of mannitol, maltolate or a derivative, protoporphyrin IX or a derivative, lactoferrin, transferrin, ferritin, bacterial siderophores belonging to the catecholate, hydroxamate, and hydroxycarboxylate groups, bacterial hemophores, and any chelators of iron.

The gallium composition may also comprise of a pharmaceutically acceptable excipient selected from the group consisting of polyols and peptides. Polyol is preferably selected from the group consisting of sucrose, trehalose, glucose, raffinose, sorbose, melezitose, glycerol, fructose, mannose, maltose, lactose, arabinose, xylose, ribose, rhamnose, galactose, glucose, mannitol, xylitol, erythritol, threitol, dextrose, fucose, polyaspartic acid, inositol hexaphosphate (phytic acid), sialic acid, or N-acetylneuraminic acid. Peptides are preferably selected from the group consisting of a tripeptide comprising two leucines and an amino acid selected from the list consisting of leucine, valine, isoleucine, tryptophan, alanine, methionine, phenylalanine, tyrosine, histidine, and proline. Peptides may also be selected from a group consisting of di- and tri-peptides, such as di-leucine, tri-leucine or their derivatives.

In certain embodiments, the gallium composition may also include other excipients, such as proteins, surfactants, and polymers. Preferred proteins are human serum albumin and recombinant human serum albumin. Surfactants are chosen from a group consisting of polyethylene, polypropylene glycol, polyethylene glycol sorbitan monolaurate, or polyoxyethylene sortiban monooleate. Examples of polymers, selected from both biopolymers and synthetic polymers, include alginic acid, alginates, heparin, heparin sulfates, hyaluronic acid, hyaluronates, chitosan, chitin, starch, starch derivatives, carboxymethyl starch, hydroxyethyl starch (HES), dextran, polyvinyl pyrrolidone (PVP), gelatin, collagen, chrondroitin sulfate, or polyvinyl alcohol.

The present invention includes methods of preparing a liquid gallium composition comprising a therapeutically effective amount of gallium. Said liquid gallium composition is characterized as having at least a 1:1 counterion-to-gallium molar ratio, to increase the solubility of gallium and to prevent its precipitation upon delivery. The counterion content, as well as the other excipients listed above, may also be adjusted to modify the mass median aerodynamic diameter (MMAD) and nebulization time by enhancing the viscosity and time required for droplet evaporation.

Furthermore, the present invention includes methods of preparing a dry powder comprising a therapeutically effective amount of gallium. The dry powder can be produced either by spray drying or freeze drying. Said dry powder is characterized as having at least 95% of the mass of the powder with a particle size below 10 µm. Furthermore, the powder has an aerosol particle size distribution of from about 1.0 to 5.0 µm MMAD and a bulk density from 0.1 to 10 $g/cm^3$. The dry powder composition may be crystalline, partially crystalline, liquid-crystalline, non-crystalline or amorphous with a glass transition temperature greater than 20° C. Typically, the most desired size distribution for an aerosol prepared from a liquid formulation is the same as the most desired size distribution of dry powder particles. In other aspects, it is contemplated that the most desired size distribution for an aerosol is not the same, or need not be the same, as that for dry powder particles.

Another object of the present invention is to provide a method of treatment of pulmonary infections, using a therapeutically effective dose of gallium, caused by bacteria, viruses, fungi, or protozoa. Examples of gram-negative bacteria include but are not limited to *Escherichia coli, Klebsiella pneumoniae, Klebsiella oxytoca, Pseudomonas aeruginosa, Haemophilus influenzae, Proteus mirabilis, Enterobacter* species, *Serratia marcescens* as well as those caused by *Burkholderia cepacia, Acinetobacter baumannii, Stenotrophomonas maltophilia, Alcaligenes xylosoxidans*, and multidrug resistant *Pseudomonas aeruginosa* and *Mycobacterium tuberculosis*. Pulmonary infections may also be caused by gram-positive bacteria, including but not limited to *staphylococcus aureus, Rhodococcus equi, Staphylococcus aureus*, methycillin resistant *staphylococcus aureus* (MRSA), *Actinobacteria, Lactobacillaes, Actinomyces*, and *Clostridum*. Pulmonary infections may also be caused by viruses including but not limited to influenza virus, parainfluenza virus, respiratory syncytial virus, human metapneumovirus, corona virus family members, human immunodeficiency virus, herpes simplex virus, cytomegalovirus, SARS (Severe Acute Respiratory Syndrome) virus, Epstein-Barr virus, and the like. Pulmonary infections may also be caused by fungi including but not limited to *Histoplasma capsulatum* causing histoplasmosis, *Coccidioides immitis* causing coccidioidomycosis, *Blastomyces dermatitidis* causing blastomycosis, *Paracoccidioides brasiliensis* causing paracoccidioidomycosis, *Candida* sp. causing candidiasis, *Aspergillus* sp. causing aspergillosis, *Mucor* sp. causing mucormycosis, *Cryptococcus neoformans* causing cryptococcosis. Pulmonary infections may also be caused by protozoa including but not limited to *Entamoeba, Acanthamoeba, Balamuthia, Leishmania, Trypanosoma, Trichomonas, Lophomonas, Cryptosporidium, Cyclospora, Toxoplasma, Plasmodium, Babesia, Encephalitozoon, Enterocytozoon* and *Balantidium*.

What is provided is gallium (III) in the form of a pharmaceutically acceptable salt, comprising from about 1% by weight to about 90% by weight gallium (III) wherein the pharmaceutically acceptable salt is nitrate, citrate, chloride, or a mixture thereof. Further, what is provided is a liquid gallium (III) composition of the above-disclosed salt, wherein the citrate-to-gallium molar ratio is 1:1 or greater, and a liquid gallium (III) composition of the above-disclosed salt, wherein the citrate-to-gallium molar ratio is 2:1, as well as a liquid gallium (III) composition of the above-disclosed salt, wherein the citrate-to-gallium molar ratio is 3:1.

Moreover, what is provided is a method using the above-disclosed salt, wherein gallium (III) in the form of a pharmaceutically acceptable salt comprises of the step of administering a therapeutically acceptable dose to the lung of a patient by aerosol, as well as a method wherein the half-life of gallium is enhanced through its delivery via the pulmonary route, and, in another aspect, where the aerosol size distribution may be modulated by adjusting the osmolarity of the solution, and, in yet another aspect, the method wherein a therapeutically effective dose of gallium is administered to a patient via oral, transdermal, parenteral, vaginal, or rectal route.

In another aspect of the method, what is provided is a method of treatment using the composition of the above-disclosed salt for pulmonary infections caused by: gram-negative bacteria including but not limited to *Escherichia coli, Klebsiella pneumoniae, Klebsiella oxytoca, Pseudomonas aeruginosa, Haemophilus influenzae, Proteus mirabilis, Enterobacter* species, *Serratia marcescens* as well as those caused by *Burkholderia cepacia, Acinetobacter baumannii, Stenotrophomonas maltophilia, Alcaligenes xylosoxidans*, and multidrug resistant *Pseudomonas aeruginosa* and *Mycobacterium tuberculosis* and/or gram-positive bacteria *Staphylococcus aureus, Rhodococcus equi, Staphylococcus aureus*, methycillin resistant *Staphylococcus aureus* (MRSA), *Actinobacteria, Lactobacillaes, Actinomycies*, and *Clostridum*. Moreover, what is provided is the above method, wherein the method is suitable for treatment of infections caused by gram-negative bacteria in patients with cystic fibrosis, bronchiectasis, chronic obstructive pulmonary diseases (COPD), or in the patients on ventilators, as well as the above method, wherein the method is suitable for treatment of pulmonary infections caused by viruses, fungi, or protozoa. In another aspect, what is contemplated is the above method, wherein the gallium (III) liquid composition is administered in conjunction with antibiotics such as aztreonam, vancomycin, tobramycin, amikacin, amphotericin B, colistin, meropenem, ciprofloxacin, and piperacillin.

In yet another aspect, what is provided is a liquid composition disclosed above, wherein gallium (III) composition further comprises of a complexing agent selected from mannitol, maltolate, protoporphyrin IX or its derivative, bacterial siderophores belonging to the catecholate, hydroxamate, and hydroxycarboxylate groups, bacterial hemophores, any chelators of iron, or a mixture thereof. Additionally, what is provided is the above liquid composition of gallium (III) in the form of a pharmaceutically acceptable salt, wherein the citrate-to-gallium molar ratio is 1:1 or greater, as well as the above liquid composition of liquid gallium (III) composition, wherein the citrate-to-gallium molar ratio is 2:1, and additionally, the above liquid gallium (III) composition, wherein the citrate-to-gallium molar ratio is 3:1.

Alternatively, what is provided is the above method, wherein gallium (III) in the form of a pharmaceutically acceptable salt comprises of the step of administering a therapeutically acceptable dose to the lung of a patient by aerosol. Furthermore, what is contemplated is the above liquid composition and method, wherein the half-life of gallium is enhanced through its delivery via the pulmonary route, as well as the above liquid gallium composition and method, in which the aerosol size distribution may be modulated by adjusting the osmolarity of the solution, and additionally, the above liquid composition and method, wherein a therapeutically effective dose of gallium is administered to a patient via oral, transdermal, parenteral, vaginal, or rectal route.

The invention, in another aspect, provides a method of treatment using the composition (disclosed above) for pulmonary infections caused by: a) gram-negative bacteria including but not limited to *Escherichia coli, Klebsiella pneumoniae, Klebsiella oxytoca, Pseudomonas aeruginosa, Haemophilus influenzae, Proteus mirabilis, Enterobacter* species, *Serratia marcescens* as well as those caused by *Burkholderia cepacia, Acinetobacter baumannii, Stenotrophomonas maltophilia, Alcaligenes xylosoxidans*, and multidrug resistant *Pseudomonas aeruginosa* and *Mycobacterium tuberculosis* and/or, b) gram-positive bacteria *Staphylococcus aureus, Rhodococcus equi, Staphylococcus aureus*, methycillin resistant *Staphylococcus aureus* (MRSA), *Actinobacteria, Lactobacillaes, Actinomycies*, and *Clostridium*.

The invention also provides the above method suitable for treatment of infections caused by gram-negative bacteria in patients with cystic fibrosis, bronchiectasis, chronic obstructive pulmonary diseases (COPD), or in the patients on ventilators, as well as a method suitable for treatment of pulmonary infections caused by viruses, fungi, or protozoa. Further, what is provided is the above method, wherein the gallium (III) liquid composition is administered in conjunction with antibiotics such as aztreonam, vancomycin, tobramycin, amikacin, amphotericin B, colistin, meropenem, ciprofloxacin, and piperacillin.

Regarding dry powder embodiments, what is provided is a dry powder composition of gallium (III) in the form of a pharmaceutically acceptable salt, wherein the citrate-to-gallium molar ratio is 1:1 or greater, as well as a dry powder composition, wherein at least about 95% of the mass of the powder has a particle size below 100 μm, and the above dry powder composition, wherein at least about 95% of the mass of the powder has a particle size below 10 μm, and also the above dry powder composition, wherein said dry powder particles have an aerosol particle size distribution of from about 1.0 to 10.0 μm MMAD, and also the above dry powder composition, wherein said dry powder particles have an aerosol particle size distribution of from about 1.0 to 5.0 μm MMAD, and in yet another aspect of the present invention what is provided is the above dry powder composition, wherein said dry powder is characterized by a delivered dose of greater than about 10% using commercially available dry powder inhalers, and pressured metered dose inhalers, or wherein said dry powder is characterized by a delivered dose of greater than about 30% using commercially available dry powder inhalers, or wherein the crystallinity of said dry powder can be modified with the addition of suitable excipients, or wherein the release of gallium from the dry powder can be modified by the degree of crystallinity, or wherein citrate is the excipient, or wherein the half-life of gallium is enhanced through the delivery of gallium composition via the pulmonary route, or wherein the dry powder is produced by spray drying, or wherein the dry powder is produced by freeze drying followed by milling.

In another methods embodiment of the present invention, what is provided is the above method of treatment using a composition disclosed above for pulmonary infections caused by: a) gram-negative bacteria including but not limited to *Escherichia coli, Klebsiella pneumoniae, Klebsiella oxytoca, Pseudomonas aeruginosa, Haemophilus influenzae, Proteus mirabilis, Enterobacter* species, *Serratia marcescens* as well as those caused by *Burkholderia cepacia, Acinetobacter baumannii, Stenotrophomonas maltophilia, Alcaligenes xylosoxidans*, and multidrug resistant *Pseudomonas aeruginosa* and *Mycobacterium tuberculosis* and/or b) gram-positive bacteria *Staphylococcus aureus, Rhodococcus equi, Staphylococcus aureus*, methycillin resistant *Staphylococcus aureus* (MRSA), *Actinobacteria, Lactobacillaes, Actinomycies*, and *Clostridum*. Furthermore, what is provided is the above method suitable for treatment of infections caused by the gram-negative bacteria in patients with cystic fibrosis, bronchiectasis, chronic obstructive pulmonary diseases (COPD), or in the patients on ventilators, and the above method suitable for treatment of pulmonary infections caused by the viruses, fungi, or protozoa, and the above method of treatment delivering said gallium (III) dry powder aerosol composition (a composition disclosed above) to the lung of a patient in need thereof by a nebulizer or a dry powder or metered dose inhaler.

In yet another aspect, what is provided is the above method, wherein a dose of gallium (III) dry powder aerosol and frequency of delivery for effective treatment of pulmonary infection is determined by a level of gallium (III) in a patient's sputum, and what is also provided is the above method, wherein the dry powder formulation is delivered no more than three times a day, provided that if the dry powder is delivered more than twice a day, a total dose of gallium (III) not higher than 500 mg/day is delivered, and what is further provided by the present invention is the above method, wherein the gallium (III) dry powder composition (as described above) is administered in conjunction with antibiotics such as aztreonam, vancomycin, tobramycin, amikacin, amphotericin B, colistin, meropenem, ciprofloxacin, and piperacillin. Moreover, yet another embodiment of the above dry powder composition and method provides that a therapeutically effective dose of gallium is administered to a patient via oral, transdermal, parenteral, vaginal, or rectal route.

Also, the above composition further comprises a pharmaceutically acceptable excipient selected from the group consisting of: a) polyols such as sucrose, trehalose, glucose, raffinose, sorbose, melezitose, glycerol, fructose, mannose, maltose, lactose, arabinose, xylose, ribose, rhamnose, galactose, glycose, mannitol, xylitol, erythritol, threitol, dextrose, fucose, polyaspartic acid, inositol hexaphosphate (phytic acid), sialic acid, N-acetylneuraminic acid-lactose, and sorbitol; b) amino acids selected from the group consisting of leucine, valine, isoleucine, tryptophan, alanine, methionine, phenylalanine, tyrosine, histidine, proline, their derivatives, and a mixture thereof; c) amino acids comprising a tri-peptide comprised of two leucines and an amino acid selected from the group consisting of leucine, valine, isoleucine, tryptophan, alanine, methionine, phenylalanine, tyrosine, histidine, and proline; d) di- and tri-peptides such as di-leucine, tri-leucine and their derivatives; proteins such as transferrin, lactoferrin, human serum albumin, and recombinant human serum albumin; e) organic acid salts such as citric acid or citrate, tartaric acid or tartrate, lactic acid or lactate; f) surfactant block co-polymers of polyethylene and polypropylene glycol, polyethylene glycol sorbitan monolaurate, and polyoxyethylenesorbitan monooleate; g) polysaccharides such as alginic acid, alginates, heparin, heparin sulfates, hyaluronic acid, hyaluronates, chitosan, chitin, starch, starch derivatives, carboxymethyl starch, hydroxyethyl starch (HES), and dextran; h) polymers such as polyvinyl pyrrolidone (PVP), gelatin, collagen, chrondroitin sulfate, and polyvinyl alcohol (PVA).

In yet another aspect, what is provided is the above dry powder composition, further comprising a pharmaceutically acceptable agent to enhance aerosol properties including amino acids selected from leucine, L-leucine, D-leucine, DL-leucine, isoleucine, trileucine, valine, alanine, their derivatives, and mixtures thereof, comprising not more than 90% by weight of the dry powder, and the above dry powder composition, wherein the amino acid comprises at least about 5% of the mass of the dry powder, and the above dry powder composition, wherein the amino acid comprises at least about 10% of the mass of the dry powder, and the above dry powder composition, wherein at least about 95% of the mass of the powder has a particle size below 100 μm, and also the above dry powder composition, wherein at least about 95% of the mass of the powder has a particle size below 10 μm, and additionally the above dry powder composition, wherein said dry powder particles have an aerosol particle size distribution of from about 1.0 to 10.0 μm MMAD, and in another aspect, the above dry powder composition, wherein said dry powder particles have an aerosol particle size distribution of from about 1.0 to 5.0 μm MMAD.

Moreover, what is provided is the above dry powder composition, wherein said dry powder is characterized by a delivered dose of greater than about 10% using commercially available dry powder inhalers, and the above dry powder composition, wherein said dry powder is characterized by a delivered dose of greater than about 30% using commercially available dry powder inhalers, and the above dry powder composition, wherein the crystallinity of said dry powder can be modified with the addition of suitable excipients, and the above dry powder composition, wherein the release of gallium from the dry powder can be modified by the degree of crystallinity, and the above dry powder composition, wherein citrate is the preferred excipient, and the above dry powder composition, wherein the half-life of gallium is enhanced through the delivery of gallium composition via the pulmonary route, and also the above dry powder composition, wherein the dry powder is produced by spray drying, and additionally, the above dry powder composition, wherein the dry powder is produced by freeze drying followed by milling.

Regarding methods, the present invention in some aspects provides a method of treatment using the above composition, for pulmonary infections caused by: a) gram-negative bacteria including but not limited to *Escherichia coli, Klebsiella pneumoniae, Klebsiella oxytoca, Pseudomonas aeruginosa, Haemophilus influenzae, Proteus mirabilis, Enterobacter* species, *Serratia marcescens* as well as those caused by *Burkholderia cepacia, Acinetobacter baumannii, Stenotrophomonas maltophilia, Alcaligenes xylosoxidans*, and multidrug resistant *Pseudomonas aeruginosa* and *Mycobacterium tuberculosis* and/or b) gram-positive bacteria *Staphylococcus aureus, Rhodococcus equi, Staphylococcus aureus*, methycillin resistant *Staphylococcus aureus* (MRSA), *Actinobacteria, Lactobacillaes, Actinomycies*, and *Clostridium*. Moreover, what is provided is the above method, suitable for treatment of infections caused by the gram-negative bacteria in patients with cystic fibrosis, bronchiectasis, chronic obstructive pulmonary diseases (COPD), or in the patients on ventilators, and what is contemplated is the above method suitable for treatment of pulmonary infections caused by the viruses, fungi, or protozoa, and what is contemplated is the above method of treatment that involves delivering said gallium (III) dry powder aerosol composition according to the lung of a patient in need thereof by a nebulizer or a dry powder or metered dose inhaler, and what is provided is the above method, wherein a dose of gallium (III) dry powder aerosol and frequency of delivery for effective treatment of pulmonary infection is determined by a level of gallium (III) in a patient's sputum, and in yet another aspect, the present invention provides the above method, wherein the dry powder formulation is delivered no more than three times a day, provided that if the dry powder is delivered more than twice a day, a total dose of gallium (III) not higher than 500 mg/day is delivered. In yet another aspect, what is disclosed is use in the manufacture of a medicament for the above method of treatment, and use in the manufacture for the above method of administering.

Regarding methods, the invention provides the above method, wherein the gallium (III) dry powder composition (according to one or more of the above embodiments) is administered in conjunction with antibiotics such as aztreonam, vancomycin, tobramycin, amikacin, amphotericin B, colistin, meropenem, ciprofloxacin, and piperacillin.

Regarding the above-disclosed dry powder compositions and related methods, what is provided is a therapeutically effective dose of gallium is administered to a patient via pulmonary, oral, transdermal, parenteral, vaginal, or rectal route.

The present invention, in a preferred embodiment, provides a pharmaceutical formulation that comprises a solution of gallium (III) and an anion or a complexing agent that complexes gallium, or that comprises a dry powder derived from said solution, wherein the solution comprises an anti-microbially effective concentration of gallium (III). In another preferred embodiment, what is provided is the above pharmaceutical formulation, wherein the formulation includes citrate, and the molar ratio of citrate to gallium is greater than 1:1. In yet another preferred embodiment, what is provided is the above formulation, where the formulation is an aerosol, and where the molar ratio of citrate to gallium is 1:1.

What is provided is a pharmaceutical formulation comprising a solution, where the molar ratio of maltolate:gallium is greater than 1:1, or where the ratio of isomaltolate:gallium is greater than 1:1, or where the ratio is greater than 1.25:1, or where the ratio is greater than 1.5:1, or where the ratio is greater than 1.75:1, or where the ratio is greater than 2:1, and the like. What is also encompassed is a pharmaceutical formulation comprising a dry powder, where the dry powder is derived from a solution, and where the solution contains the above-disclosed molar ratio of maltolate:gallium or of isomaltolate:gallium. Moreover, what is provided a pharmaceutical formulation that does not contain maltolate or does not contain isomaltolate.

The present invention provides a pharmaceutical formulation that comprises, or is dry powder that is derived from, a solution of gallium (III) and an anion or a complexing agent that complexes gallium, wherein the solution comprises an anti-microbially effective concentration of gallium (III), and wherein the molar ratio of the anion to gallium, where the anion is citrate (in the embodiment where the anion is citrate), is greater than 1:1.

Also, the pharmaceutical formulation comprises, or is a dry powder that is derived from, a solution of gallium (III) and an anion or a complexing agent that complexes gallium, wherein the solution comprises an anti-microbially effective concentration of gallium (III), and where the formulation includes citrate, the molar ratio of citrate to gallium is greater than 1:1.

In an aerosol embodiment of the above pharmaceutical formulation, what is provided is an aerosol where the molar ratio of citrate to gallium is 1:1, or where the molar ratio of citrate to gallium is about 1:1, or where the molar ratio of citrate to gallium is in the range of 0.90-1.10 to 1.

Moreover, what is provided is the above pharmaceutical formulation of, wherein adding a volume of the solution in a bolus to a ten fold greater volume of a biological fluid that is human blood plasma or an extracellular lung fluid, does not result in turbidity, where turbidity is assessed visually after adding the solution to the biological fluid.

In another aspect, what is provided is the above pharmaceutical formulation, wherein adding a volume of the pharmaceutical formulation in a bolus to a ten fold greater volume of a biological fluid that is human blood plasma or an extracellular lung fluid, does not result in turbidity, where turbidity is assessed after adding the solution to the biological fluid.

In another aspect, the invention provides the above pharmaceutical formulation, wherein the anion or complexing agent is citrate.

Moreover, yet another embodiment provides one or more of the above formulations, wherein the molar ratio of citrate to gallium is at least 1.1:1, at least 1.2:1, at least 1.3:1, at least 1.4:1, at least 1.5:1, at least 1.6:1, at least 1.7:1, at least 1.8:1, at least 1.0:1, at least 2:1, and the like.

What is also contemplated, is one or more of the above embodiments, wherein the molar ratio of citrate to gallium is not more than 5:1, not more than 4:1, not more than 3:1, not more than 2.5:1, not more than 2.0:1, or not more than 1.5:1. Moreover, what is contemplated is one or more of the embodiments with a reduced level of nitrate, or a non-detectable of nitrate, for example, wherein the molar ratio of nitrate:gallium is lower than 0.2:1, or lower than 0.1:1. In yet another aspect, what is provided is one or more of the above pharmaceutical formulation embodiments, that is a solution, a dry powder, a gel, an aerosol, or that is not a solution.

In yet another aspect, what is provided is the above pharmaceutical formulation, that comprises a complexing agent selected from mannitol, maltolate, protoporphyrin IX or its derivative, siderophores of the catecholate, hydroxamate, and hydroxycarboxylate groups, bacterial hemophores, an iron chelator, or a mixture thereof. The siderophore can be, for example, bacterial or fungal. Moreover, what is provided is a device configured for providing an aerosol, wherein the device comprises one or more of the pharmaceutical formulations disclosed herein, and wherein the device is capable of delivering an aerosol of the pharmaceutical formulation to the lungs, gastrointestinal tract, or skin. The device can be one that provides metered dose delivery.

In yet another aspect, what is provided is a pharmaceutical formulation disclosed herein, that contains gallium citrate, wherein a standard test at pH 10.0 and using about 234.6 mM gallium nitrate is used to test for precipitation, and wherein the molar ratio of citrate:gallium in the pharmaceutical formulation is sufficient to prevent formation of a precipitate under the standard test, and wherein formation of a precipitate can be assessed in the standard test condition by mixing 234.6 mM of gallium nitrate with sodium citrate, and wherein the lack or presence of a precipitate is determined visually.

Moreover, in an embodiment that comprises citrate, what is provided is one or more of the above pharmaceutical formulations that comprises a solution of gallium (III) and citrate, wherein the solution comprises an anti-microbially effective concentration of gallium (III), and wherein the molar ratio of citrate to gallium is greater than 1:1.

The following concerns a test that adds a solution in a bolus. In another aspect, what is contemplated is the above pharmaceutical formulation, wherein adding a volume of the formulation in a bolus to a ten fold greater volume of a biological fluid that is human plasma or an extracellular lung fluid, does not result in turbidity, where turbidity is assessed visually after adding the solution to the biological fluid.

The following concerns a test that adds a formulation in a bolus. In another aspect, what is contemplated is the above pharmaceutical formulation, wherein adding a volume of the formulation in a bolus to a ten fold greater volume of a biological fluid that is human plasma or an extracellular lung fluid, does not result in turbidity, where turbidity is assessed visually after adding the solution to the biological fluid.

What is also provided a pharmaceutical formulation as disclosed above, wherein the molar ratio of citrate to gallium is at least 1.1:1; and a pharmaceutical formulation as disclosed above, wherein the molar ratio of citrate to gallium is not more than 5:1. In an embodiment of reduced nitrate or non-detectable nitrate, what is contemplated is one of the above pharmaceutical formulations, wherein the molar ratio of nitrate:gallium is lower than about 0.2:1, or lower than 0.1:1.0.

In a methods embodiment of the present invention, what is provided is a method for treating or preventing an infection comprising administering one of the pharmaceutical formulations as disclosed above, to a subject having the infection or at risk for the infection. Moreover, what is provided is the above method, wherein the infection comprises a pulmonary infection; or the above method, wherein the pharmaceutical composition is administered by inhalation to the lung, wherein the gallium of the pharmaceutical composition has a residence time in the lung, and wherein the residence time in the lung is at least 5-fold longer than the residence time in the lung of gallium administered intravenously, wherein the number of moles of gallium inhaled is about the same as the number of moles administered intravenously, or wherein the half-life for the residence time in the lung is at least 16 hours, at least 18 hours, at least 21 hours, at least 24 hours, at least 27 hours, at least 30 hours, at least 33 hours, at least 36 hours, and the like. What is also contemplated, is the above method where the half-life for the residence time in the lung is at least 10 hours, at least 11 hours, at least 12 hours, at least 13 hours, at least 14 hours, at least 15 hours, and so on. In another aspect, what is disclosed is use in the manufacture of a medicament for the above method of treatment, and use in the manufacture for the above method of administering.

What is also contemplated is the above method, wherein the infection comprises a gram positive bacterium or a gram negative bacterium; or the above method, wherein the infection comprises: a. A gram-negative bacterium that is *Escherichia coli, Klebsiella pneumoniae, Klebsiella oxytoca, Pseudomonas aeruginosa, Haemophilus influenzae, Proteus mirabilis, Enterobacter* species, *Serratia marcescens, Burkholderia cepacia, Acinetobacter baumannii, Stenotrophomonas maltophilia, Alcaligenes xylosoxidans*, multidrug resistant *Pseudomonas aeruginosa*, or *Mycobacterium tuberculosis*, or b) A gram-positive bacterium that is *Staphylococcus aureus, Rhodococcus equi, Staphylococcus aureus*, methycillin resistant *Staphylococcus aureus* (MRSA), *Actinobacteria, Lactobacillales, Actinomycies*, or *Clostridium*; or the above method, wherein the infection is a pulmonary infection that is caused by a viruses, fungus, or protozoan; or the above method, wherein the administering is by way of a route that is oral, inhalation, intravenous, topical, ocular, intraocular, a transfusion, transdermal, parenteral, vaginal, or rectal; or the above method, wherein the subject has cystic fibrosis, bronchiectasis, chronic obstructive pulmonary diseases (COPD), or is a subject on a ventilator.

In an embodiment comprising dry powder, what is provided is a pharmaceutical formulation comprising a dry powder composition of gallium (III) particles having a pharmaceutically acceptable mass median aerodynamic diameter (MMAD), wherein the mean particle size is lower than 10 micrometers. Also, what is contemplated is the above pharmaceutical formulation, wherein the particles have a MMAD that is equal or lower than 5 micrometers; or wherein the particles have a MMAD that is between 1 to 5 micrometers; or one or more of the above pharmaceutical formulations, that comprises an amino acid, an oligopeptide, a monosaccharide, an oligosaccharide, or a mixture thereof; or that comprises one or more of citrate, mannitol, leucine, or trileucine, and where the mean particle size is 10 micrometers or less; or that comprises a dry powder formulation of Table 2, wherein the MMAD is 10 micrometers or less; or in other embodiments, wherein the amino acid is leucine, the oligopeptide is trileucine, and the monosaccharide is mannitol; and in still additional embodiments, the above pharmaceutical formulation that comprises one or more of citrate, mannitol, leucine, and trileucine, wherein the relative molar ratios of gallium, citrate, mannitol, leucine, and trileucine, are about that found in one of the formulations disclosed in Table 13, and the mean particle size is under 10 micrometers; and a pharmaceutical formulation as above, wherein the molar ratio of gallium to leucine is in the range of 1:0.5 to 1:2.5, and the MMAD is under 10 micrometers; or wherein the molar ratio of gallium to trileucine is in the range of 1:0.1 to 1:0.8, and the MMAD is under 10 micrometers; or wherein the molar ratio of nitrate: gallium is lower than about 0.1:1.0.

Regarding complexing agents, the present invention provides the above pharmaceutical formulation, that comprises a complexing agent selected from mannitol, maltolate, protoporphyrin IX or its derivative, siderophores of the catecholate, hydroxamate, and hydroxycarboxylate groups, bacterial hemophores, an iron chelator, or a mixture thereof.

Regarding excipients, what is provided is one or more of the above pharmaceutical formulations, further comprising a pharmaceutically acceptable excipient selected from: a) a polyol that is sucrose, trehalose, glucose, raffinose, sorbose, melezitose, glycerol, fructose, mannose, maltose, lactose, arabinose, xylose, ribose, rhamnose, galactose, glycose, mannitol, xylitol, erythritol, threitol, dextrose, fucose, polyaspartic acid, inositol hexaphosphate (phytic acid), sialic acid, N-acetylneuraminic acid-lactose, or sorbitol; b) an amino acid that is leucine, valine, isoleucine, tryptophan, alanine, methionine, phenylalanine, tyrosine, histidine, proline, their derivatives, and a mixture thereof; c) a tri-peptide comprised of two leucines and an amino acid, selected from leucine, valine, isoleucine, tryptophan, alanine, methionine, phenylalanine, tyrosine, histidine, and proline; d) a protein that is transferrin, lactoferrin, human serum albumin, or recombinant human serum albumin; e) an organic acid salts that is citric acid or citrate, tartaric acid or tartrate, or lactic acid or lactate; f) a surfactant block co-polymers of polyethylene, polypropylene glycol, polyethylene glycol sorbitan monolaurate, or polyoxyethylenesorbitan monooleate; g) a polysaccharide that is alginic acid, alginates, heparin, heparin sulfates, hyaluronic acid, hyaluronates, chitosan, chitin, starch, starch derivatives, carboxymethyl starch, hydroxyethyl starch (HES), or dextran; h) a polymer that is polyvinyl pyrrolidone (PVP), gelatin, collagen, chrondroitin sulfate, or polyvinyl alcohol (PVA).

In a device embodiment of the present invention, what is provided is an aerosol, wherein the device comprises the pharmaceutical formulation as disclosed above, and wherein the device is capable of providing an aerosol of the pharmaceutical composition to the lungs, gastrointestinal tract, or skin; or the above device wherein the device provides metered dose delivery.

In yet another methods embodiment, what is provided is a method for treating or preventing an infection comprising administering the pharmaceutical formulation, as disclosed above, to a subject having the infection or at risk for the infection; or the above method, wherein the infection comprises a pulmonary infection; or the above method, wherein the infection comprises a gram positive bacterium or a gram negative bacterium; and also the above method, wherein the infection comprises: a) A gram-negative bacterium that is *Escherichia coli, Klebsiella pneumoniae, Klebsiella oxytoca, Pseudomonas aeruginosa, Haemophilus influenzae, Proteus mirabilis, Enterobacter* species, *Serratia marcescens, Burkholderia cepacia, Acinetobacter baumannii, Stenotrophomonas maltophilia, Alcaligenes xylosoxidans*, multidrug resistant *Pseudomonas aeruginosa*, or *Mycobacterium tuberculosis*, or b) A gram-positive bacterium that is *Staphylococcus aureus, Rhodococcus equi, Staphylococcus aureus*, methycillin resistant *Staphylococcus aureus* (MRSA), *Actinobacteria, Lactobacillales, Actinomycies*, or *Clostridium*; or the above method, wherein the infection is a pulmonary infection that is caused by a viruses, fungus, or protozoan; or the above method, wherein the administering is by way of a route that is oral, inhalation, intravenous, topical, ocular, intraocular, a transfusion, transdermal, parenteral, vaginal, or rectal; or the above method, wherein the subject has cystic fibrosis, bronchiectasis, chronic obstructive pulmonary diseases (COPD), or is a patient on a ventilator. In another aspect, what is disclosed is use in the manufacture of a medicament for the above method of treatment, and use in the manufacture for the above method of administering.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "a buffer" can include mixtures of buffers, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

The term "about", as used herein, indicates the value of a given quantity can include quantities ranging within 50% of the stated value, within 25% of the stated value, within 10% of the stated value, within 5% of the value, or within 1% of the value.

As used herein, the terms "solution and suspension" and "liquid formulation" are often used interchangeably.

"Therapeutically effective dose" or "therapeutically effective amount" refers to the amount of compound sufficient to treat, manage or ameliorate a disease or disorder caused by pathogenic organisms in a subject. A therapeutically effective dose or therapeutically effective amount can refer to the amount of the compound sufficient to reduce the number of pathogenic microorganisms, to suppress the growth of pathogenic microorganisms, or to kill pathogenic microorganisms at the affected sites or in the bloodstream of a subject. The therapeutically effective dose or therapeutically effective amount will vary depending on the compound, the disease and its severity, and the age, weight, physical condition and responsiveness of the individual to be treated.

"Pharmaceutically acceptable" refers to those active agents, salts, and excipients which are, within the scope of sound medical judgment, suitable for use in contact with the tissues or humans and lower animals without undue toxicity, irritation, allergic response and the like, commensurate with a reasonable benefit/risk ratio, and effective for their intended use.

BRIEF DESCRIPTION OF THE DRAWINGS

FIG. 1 shows the effect of citrate concentration on the solubility of gallium in human blood plasma. The image was taken immediately after solution containing 2:1 (left) and 1:1 (right) citrate-to-gallium molar ratio was added to human blood plasma.

FIG. 2 shows the droplet size distribution of gallium-citrate compositions aerosolized using Evo Aeroneb Go micropump nebulizer (Aeroneb, Adel, Iowa). The four compositions consisted of 1:1 citrate-to-gallium (white bars), 3:1 citrate-to-gallium (black bars), 1:1 citrate-to-gallium at three times the dose (grey bars), and 1:1 citrate-to-gallium at three times the dose handled at 75% RH (dashed bars).

FIG. 3 shows the particle size distribution of various gallium-containing compositions. The four compositions consisted of gallium nitrate (white bars), gallium nitrate with sodium citrate (1:1 molar ratio, black bars), gallium nitrate with sodium citrate (1:1 molar ratio) and L-leucine (0.4%, w/v, gray bars), and gallium nitrate with sodium citrate (1:1 molar ratio), mannitol (0.6%, w/v), and L-leucine (0.4%, w/v, dashed bars). The term "molar ratio" in this context refers to the molar ratio of citrate:gallium.

FIG. 4 shows the particle size distribution of various gallium-containing compositions. The four compositions consisted of 0.4% (w/v) gallium nitrate with 0.5% (w/v) L-leucine (white bars), 1.5% (w/v) gallium nitrate with 0.4% (w/v) L-leucine (black bars), 0.4% (w/v) gallium nitrate with 0.5% (w/v) tri-leucine (gray bars), and 1.5% (w/v) gallium nitrate with 0.5% (w/v) tri-leucine (dashed bars). In all cases, the gallium composition further contained sodium citrate and mannitol at a concentration of 1.1% (w/v) and 0.6% (w/v), respectively. Tri-leucine was from Bachem, Torrance, Calif.

FIG. 5 shows the pXRD scans of spray dried gallium preparations: (a) neat gallium nitrate, (b) gallium nitrate with sodium citrate, (c) gallium nitrate with sodium citrate and mannitol, (d) gallium nitrate with sodium citrate, mannitol, and L-leucine, (e) gallium nitrate with mannitol, (f) gallium nitrate with L-leucine, and (g) gallium nitrate with sodium citrate and L-leucine. The exact compositions are shown in Table 8.

DETAILED DESCRIPTION

Figure 1:
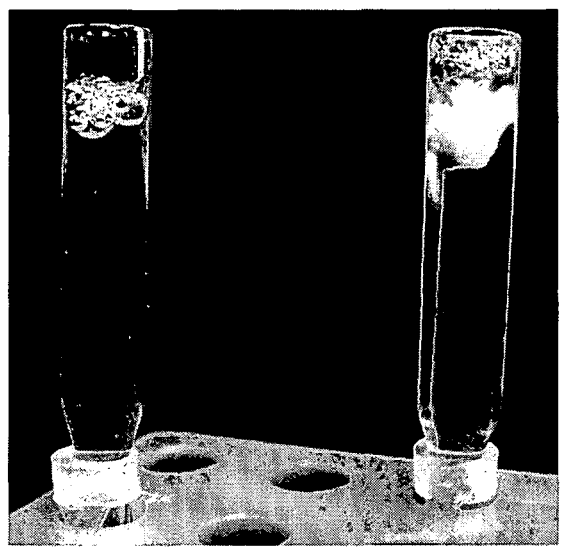

The present invention is directed to methods of preparing a gallium-containing composition for use as an antiinfective. Such composition can be administered to patients in a multitude of ways, including but not limited to pulmonary delivery and topical applications. Gallium can be given at a much lower dose compared to currently available antibiotics and has the advantage of demonstrating efficacy against a broad spectrum of bacteria. Compositions comprising gallium at a therapeutically effective dose also contains pharmaceutically acceptable excipients, the purpose of which may include: the control of release of gallium from the composition, the modulation of droplet diameter in the case of aerosol delivery using a nebulizer, and the enhancement of aerosol property of dry powder composition. Key attributes to this invention involve the identification of unique formulation combinations well suited for the delivery method of interest.

Preparing a Solution or Suspension.

The gallium-containing composition of the present invention, encompasses, but is not limited to, preparation by dissolving a therapeutically effective amount of gallium in the form of gallium nitrate salt in water and adding pharmaceutically acceptable excipients. If a different counterion to nitrate is desired, such a compound may be prepared using methods that are known to those skilled in the art. A suitable counterion includes, but is not limited to, nitrate, citrate, chloride, or a mixture thereof. In a preferred embodiment of this invention, citrate is used as the counterion. The amount of counterion, which may also act as a buffering agent, may need to be adjusted to prevent gallium precipitation, depending on the route of administration as well as the intended dose of gallium to be administered. Furthermore, the amount of counterion may be adjusted to modify the MMAD and dosing time to a suitable range, affording flexibility against variation in aerosol production for the various commercially available nebulizers.

In a particular embodiment of the current invention, the release of gallium from the administered dose is controlled by the use of pharmaceutically acceptable excipients. These excipients, or complexing agents, are known to interact strongly with gallium or gallium salt and may retard the release of gallium, and thus limit the availability of gallium to the administered site. Alternatively, if the target is different from the area of administration, the complexing agent may affect the rate of gallium transport in addition to affecting the release of gallium from the composition. Complexing agent is chosen from a group consisting of mannitol, maltolate or its derivative, protoporphyrin IX or its derivative, bacterial siderophores belonging to the catecholate, hydroxamate, and hydroxycarboxylate groups, bacterial hemophores, and any chelators of iron, or a mixture thereof. In a preferred aspect of this embodiment, mannitol is used as the complexing agent.

Polyols can be included to modify the osmolarity of the gallium-containing solution or as a bulking agent, in case of dry powder applications. Certain polyols may also be used to complex to gallium, allowing a time-release mechanism. Preferred polyols are sucrose, trehalose, glucose, raffinose, sorbose, melezitose, glycerol, fructose, mannose, maltose, lactose, arabinose, xylose, ribose, rhamnose, galactose, glycose, mannitol, xylitol, erythritol, threitol, dextrose, fucose, polyaspartic acid, inositol hexaphosphate (phytic acid), sialic acid, N-acetylneuraminic acid-lactose, and sorbitol.

Amino acids can be useful in modifying the osmolarity of the gallium-containing solution, the pH, and the surface properties of atomized droplets, and thus dried particles. Exemplary amino acids useful in this application can include leucine, valine, isoleucine, tryptophan, alanine, methionine, phenylalanine, tyrosine, histidine, proline, their derivatives, and a mixture thereof. Di- and tri-peptides such as di-leucine, tri-leucine and their derivatives, and tri-peptides comprised of two leucines and an amino acid selected from the group consisting of leucine, valine, isoleucine, tryptophan, alanine, methionine, phenylalanine, tyrosine, histidine, and proline can also be used. Amino acids that are amphiphilic or hydrophobic will concentrate on the droplet surface due to their high surface activity, and as a result, may coat the surface of gallium-containing particles.

Proteins can be included to complex with gallium and/or to modify the surface properties of atomized droplets. Suitable proteins include transferrin, lactoferrin, human serum albumin, and recombinant human serum albumin.

Polymers can be useful, e.g., in certain time-release compositions and/or to provide structural strength to sprayed products. Exemplary polymers useful in the formulations can include polyvinyl pyrrolidone (PVP), gelatin, collagen, chrondroitin sulfate, and polyvinyl alcohol (PVA).

Similar to polyols and proteins, polysaccharides can be included to complex with gallium and to act as a bulking agent, in dry powder applications. Polysaccharides can be selected from the group consisting of alginic acid, alginates, heparin, heparin sulfates, hyaluronic acid, hyaluronates, chitosan, chitin, starch, starch derivatives, carboxymethyl starch, hydroxyethyl starch (HES), and dextran.

Surfactants can be included in the formulations, e.g., to help reduce droplet sizes, enhance the solubility of other formulation constituents, and the like. Preferred surfactants in the formulations are typically non-ionic surfactants. For example, preferred surfactants can include block co-polymers of polyethylene and polypropylene glycol, polyethylene glycol sorbitan monolaurate, and polyoxyethylenesorbitan monooleate.

Typically, the pH of the gallium-containing solution is adjusted to provide a physiological pH, such as pH 7.4, of a pH ranging from about pH 4 to about pH 9, from pH 5 to pH 8, or about pH 7. Buffering capacity of the gallium-containing solution can be provided by an amino acid or a counterion.

Forming a Dry Powder.

In another aspect of the present invention, the gallium-containing compositions may be prepared as a dry powder. Dry powder production can be conducted employing a variety of methods known to those skilled in the art, which includes, but is not limited to spray drying, fluidized bed drying, supercritical fluid assisted drying, freeze drying, spray freeze drying, foam drying, and vacuum drying. Spray drying is most preferable for use in the present invention.

In an exemplary embodiment of the inventive methods, a solution containing gallium is first formulated with stabilizing excipients, then atomized from a nozzle using a pressurized gas, with or without an organic solvent serving as a liquid modifier. The atomized gallium is caused to dry into powder particles by infusing a stream of dry, heated gas co-current to the spray plume. The spray drying equipment can be any commercially available spray dryers fitted with any commercially available atomizing nozzles. The atomizing gas can be air or any other gases, preferably air, nitrogen, $CO_2$ at or near supercritical state. The gas used to evaporate the atomized solution, i.e. the drying gas, is typically heated and can be air, nitrogen, argon, or the like.

Droplets of suspensions or solutions can be dried to form particles. The drying can be conducted by any means appropriate to the droplet composition and intended use. For example, the droplets can be sprayed into a stream of drying gas, onto a drying surface, into a cold fluid to freeze the droplets for later lyophilization, and the like. Dry particles are typically not liquid and can have moisture content (e.g., residual moisture) of less than 15%, less than 10%, less than 5%, less than 3%, less than 1.5% or about 1%.

In one embodiment, the droplets are sprayed into a stream of a drying gas. For example, the drying gas can be an inert gas, such as nitrogen, at a temperature ranging from ambient temperatures to 200° C. In many cases, the stream of drying gas can enter the drying chamber to contact the droplets at a temperature of 150° C. or less, 100° C., 70° C., 50° C., 30° C. or less. The particles can be collected by settling, filtration, impact, etc. Particles can be exposed to secondary drying conditions to remove additional moisture.

The dry powder particles produced by spray drying can be room temperature stable and exhibit appropriate powder properties for deep lung delivery as well as for fabrication into other dosage formats such as oral wafers, oral thin films, capsules, tablets, etc.

Alternately, the droplets can be lyophilized to dryness. In one embodiment, the droplets are sprayed into liquid nitrogen to form frozen droplets. The droplets can settle out of the liquid nitrogen, or be removed by filtration or evaporation of the nitrogen. The collected frozen droplets can be placed in a vacuum chamber and lyophilized to form dry particles, e.g., without ever exposing the bioactive materials to high temperatures.

Once a substance enters the lungs, the body can respond to or interact with the substance in a number of ways. If the substance is a solution, the solution may dissolve into the fluids in the lungs. The solution may form a precipitate, for example, a proteinaceous precipitate, in the lungs. If the solution forms an insoluble precipitate, or if the substance itself is an insoluble substance, it may be cleared to the throat and swallowed. An insoluble particle or insoluble precipitate may produce inflammation involving alveolar macrophages and possibly long-term damage to the lungs. See, e.g., Edwards, D. A. and Dunbar, C. (2002) Annu Rev. Biomed. Eng. 4:93-107, and Poole, J. A., et al. (2009) Am. J. Physiol. Lung Cell. Mol. Physol. 296:L1085-1095.

The present invention, in some aspects, provides compositions, formulations, and methods, that reduce or prevent the conversion of soluble gallium salts to insoluble particles or to insoluble precipitates, that reduce uptake of gallium salts by macrophages, and that reduce excretion of gallium salts from the lungs.

The invention provides a composition comprising gallium (III) citrate, wherein the molar ratio of citrate to gallium is at least 1:1, at least 1.2:1, at least 1.4:1, at least 1.5:1, at least 1.8:1, at least 2.0:1, at least 2.2:1, at least 2.4:1, at least 2.6:1, at least 2.8:1, at least 3:1, at least 3.2:1, at least 3.4:1, at least 3.6:1, at least 3.8:1, at least 4:1, and the like. What is also encompassed is a range of compositions, where the range is described by a combination of a ratio disclosed above with a ratio disclosed below.

The invention also encompasses a composition comprising gallium (III) citrate, wherein the molar ratio of citrate to gallium is less than 20:1, less than 15:1, less than 10:1, less than 8:1, less than 6:1, less than 4:1, less than 3:1, less than 2:1, and so on.

For example, the invention contemplates a range of citrate:gallium of from 1:1 to 2:1. Also provided is a range of from 1:1 to 3:1. Also envisioned is a range of from 1:1 to 4:1. In another aspect, the invention contemplates a range of citrate:gallium of from 1.25:1 to 2:1. Also provided is a range of from 1.25:1 to 3:1. Also envisioned is a range of from 1.25:1 to 4:1. In yet another aspect, the invention contemplates a range of citrate:gallium of from 1.5:1 to 2:1. Also provided is a range of from 1.5:1 to 3:1. Also envisioned is a range of from 1.5:1 to 4:1, and the like.

In yet another aspect, each of the above values is provided as an approximate, that is, where the range of citrate:gallium of from about 1:1 to about 2:1. In this context, the term "about" means that each number encompasses that particular number +/−5%.

What is provided is a pharmaceutical composition comprising a salt of gallium (III) and a counterion, comprising from about 1% by weight to about 90% by weight gallium (III), from about 5% to about 90%, from about 10% to about 90%, from about 20% to about 90%, from about 40% to about 90%, from about 60% to about 90%, or from about 80% to about 90%, by weight gallium (III).

The invention provides reagents, compositions, and methods, wherein precipitation of a gallium salt is reduced by a factor of at least 10%, at least 20%, at least 30%, at least 40%, at least 50%, at least 60%, at least 70%, at least 80%, at least 90%, at least 95%, at least 99%, or by 100%. What is provided is reagents, compositions, and methods, wherein precipitation of a gallium salt is reduced to the point where turbidity cannot be detected by the naked eye, that is, to the point where the fluid containing the gallium salt is transparent and free of turbidity or cloudiness.

What is provided is a composition, formulation, reagent, salt, optionally in combination with a delivery device such as an inhaler, where precipitation or turbidity is measured by introducing the composition, formulation, reagent, salt, and the like, as a bolus (without mixing) into a biological fluid such as plasma, serum, lymph, airway surface fluid, pulmonary lymph, interstitial fluid, pulmonary interstitial fluid, and the like. Turbidity forming when a gallium salt solution contacts a biological fluid, can be measured by mixing the gallium salt solution with plasma, interstitial fluids, airway surface fluid, lymph, airway surface fluid, pulmonary lymph, pulmonary interstitial fluid, alveolar fluid, as well as these fluids from patients with cystic fibrosis, patients with a lung infection, or patients with cystic fibrosis and a lung infection.

Reduction of precipitation is relative to the absence and presence of a particular counterion or mixture of counterions. For example, what is compared can be compositions where citrate:gallium is 1:1 and where gallium citrate is 1.5:1. Or what can be compared can be a composition of citrate:gallium (1.2:1) with isocitrate:gallium (1.2:1).

The added counterion can be a combination or mixture of one or more of, e.g., citrate, nitrate, chloride, acetate, isocitrate, tartrate, and the like. The added counterion can be citrate and not any other added counterion.

The present invention, in some aspects, provides methods to reduce or avoid the formation of proteinaceous precipitates, when a solution of a gallium salt is administered. Proteinaceous precipitates can resist solubilization (see, e.g., U.S. Pat. No. 4,659,568 issued to Heilman).

For assessing the suitability of various molar ratios of citrate:gallium, or the suitability of various molar ratios of counterion:gallium, or the suitability of various molar ratios of anion:gallium, what is provided is an assay method where a solution of gallium salt is added to plasma, to an extracellular lung fluid, or another biological fluid. Plasma is a reasonable surrogate of an extracellular lung fluid such as airway surface fluid.

The ionic composition of plasma and of pulmonary extracellular fluids (also referred to as extracelluar lung fluids) have been measured (Nielson, D. W. (1986) J. Appl. Physiol. 60:972-979). The protein content and composition of plasma and of pulmonary extracellular fluids have been measured and shown to be comparable in composition (Vreim, C. E., and Staub, N. C. (1976) Am. J. Physiol. 230:376-379). Airway surface fluid, which is another term used to refer to extracellular lung fluid, has been studied (Rogers, D. F. (1994) Eur. Respir. J. 7:1690-1706; Cowley, E. A. (1997) Am. J. Physiol. 273:L895-L899). Methods for sampling lung fluids in mammals are available (Normandin, D., et al. (1990) J. Surg. Res. 48:91-98; Gray, R. D., et al. (2008) Am. J. Respir. Crit. Care Med. 178:444-452). Changes in extracellular lung fluid protein content have been reported in cystic fibrosis (Griese, M., et al. (2004) Am. J. Respir. Crit. Care Med. 170:1000-1005).

Guidance for measuring precipitation and turbidity, as it relates to drug formulations and biological fluids, is available. See, e.g., Hawe and Friess (2006) Physico-chemical lyophilization behavior of mannitol, human serum albumin formulations. Eur J Pharm Sci. 28:224-232; Martin, et al. (2007) Comparison of casein micelles in raw and reconstituted skim milk. J. Dairy Sci. 90:4543-4551; International Standards Organization, Water Quality—Determination of Turbidity, ISO 7027, Geneva, Switzerland, 1999; U.S. EPA, Methods for Chemical Analysis of Water and Wastes, Method 180.1, Determination of Turbidity by Nephelometry, Rev 2, Cincinnati, Ohio, August 1993. Turbidity meters are available from, e.g., Hanna Instruments, Woonsocket, R.I.; and LaMotte Co., Chestertown, Md. The question of turbidity exists can be determined visually, or by way of a predetermined cutoff point. Turbidity may be measured by absorbance at 660 nm, and here the cutoff point can be at absorbance equals 0.01 or greater, 0.02 or greater, 0.04 or greater, and so on. Turbidity can be measured with or without mechanical dispersion prior to spectrophotometric or turbidimetric measurement of the suspension or solution that is to be assayed.

In formulations of gallium citrate, the invention contemplates various ratios of citrate:gallium. Formulations where the ratio of citrate:gallium is high can result in undesired effects on the iron citrate receptors of microorganisms. An excess amount free citrate may compete for binding of gallium-citrate on citrate receptors of some microorganisms. An upper limit to the ratio of citrate:gallium, can be arrived at by assays sensitive to the activity of the iron citrate receptor. Also, an optimal ratio of citrate:gallium, can be arrived at with guidance from assays sensitive to the activity of the iron citrate receptor.

Guidance for measuring activities of iron citrate receptors, and for measuring the inhibition of these receptors, is available. See, e.g., Marshall, et al. (2009) Microbiology. 155:305-315; Takemura, et al. (2003) J. Dairy Sci. 86:133-137; Moody, M. D. and Dailey, H. A. (1985) J. Bacteriol. 161: 1074-1079.

Methods for measuring nitrate are available, for example, see, Dunphy, M. J., et al. (1990) Analyt. Biochem. 184:381-387; Miranda, K. M, et al. (2001) Nitric Oxide 5:62-71; Schild, J. and Klemme, J. H. (1985) Z. Naturforsch C. 40:134-137.

Ammonium ions may produce toxic or untoward reactions in the body. In a preferred embodiment, what is provided a composition, formulation, reagent, salt, optionally in combination with a delivery device such as an inhaler, and methods, of gallium and a counterion, that contains less than 100 mM ammonium ion, 80 mM, 60 mM, 50 mM, 40 mM, 20 mM, 10 mM, 5 mM, 2 mM, 1.0 mM, 0.8 mM, 0.6 mM, 0.5 mM, 0.4 mM, 0.2 mM, 0.15 mM, 0.10 mM, 0.08 mM, 0.06 mM, 0.05 mM, 0.04 mM, 0.03 mM, 0.025 mM, 0.02 mM, 0.015 mM, 0.010 mM, 0.005 mM, 0.004 mM, 0.003 mM, 0.002 mM, 0.0015 mM, or 0.001 mM ammonium ion.

High concentrations of gallium salts, such as gallium citrate, may be relatively insoluble, or may be substantially insoluble. The invention provides a pharmaceutical formulations or compositions wherein the concentration of gallium (III) is less than 1000 mM, less than 800 mM, less than 600 mM, less than 400 mM, less than 200 mM, less than 150 mM, less than 125 mM, less than 100 mM, less than 80 mM, less than 60 mM, less than 40 mM, or less than 20 mM.

What is provided is a composition, formulation, reagent, salt, optionally in combination with a delivery device such as an inhaler, and methods, of gallium and a counterion, such as citrate, wherein the molar ratio of citrate:gallium in the formulation is such that inhibition of an iron citrate receptor is less than 100% inhibition, less than 75% inhibition, less than 50% inhibition, less than 25% inhibition, less than 15% inhibition, less than 10% inhibition, less than 5% inhibition, less than 2% inhibition, less than 1% inhibition, and the like.

The invention provides is a composition, formulation, reagent, salt, optionally in combination with a delivery device such as an inhaler, and methods, and the like, that encompass gallium, where the gallium is not gallium-67, where the gallium is not gallium-68, where the gallium is free of gallium-67, and/or where the gallium is free of gallium-68.

In another aspect, what is provided is a composition, formulation, reagent, salt, optionally in combination with a delivery device such as an inhaler, and methods, wherein the mean droplet size is about 0.2, 0.4, 0.6, 0.8, or 1.0 micrometers. Also available is a composition or formulation where the mean droplet size is about 2, 5, 10, 15, 20, 25, 30, 35, 40, 45, 50, 60, 70, 80, 90, or 100 micrometers.

Moreover, what is provided is a composition, formulation, reagent, salt, optionally in combination with a delivery device such as an inhaler, and methods, where 90% of the droplets have a size smaller than about 0.2, 0.4, 0.6, 0.8, 1.0, 1.2, 1.6, or 1.8 micrometers. In yet another aspect, what is provided is a composition or formulation where 90% of the droplets have a size smaller than about 2, 5, 10, 15, 20, 25, 30, 35, 40, 45, 50, 60, 70, 80, 90, or 100 micrometers.

Furthermore, what is provided is a composition, formulation, reagent, salt, optionally in combination with a delivery device such as an inhaler, and methods, where 50% of the droplets have a size smaller than about 0.2, 0.4, 0.6, 0.8, 1.0, 1.2, 1.6, or 1.8 micrometers. In still another aspect, what is provided is a composition or formulation where 50% of the droplets have a size smaller than about 2, 5, 10, 15, 20, 25, 30, 35, 40, 45, 50, 60, 70, 80, 90, or 100 micrometers. In this context, the term "about" means the number +/−5%.

The following concerns an upper limit to molar concentrations of the gallium solutions of the present invention. The following also concerns an upper limit to molar concentrations of the pharmaceutical formulations of gallium solutions of the present invention. In some aspect, the concentration of gallium is 1000 micromolar ($\mu$M) or less, 800 $\mu$M or less, 600 $\mu$M or less, 500 $\mu$M or less, 400 $\mu$M or less, 300 $\mu$M or less, 200 $\mu$M or less, 150 $\mu$M or less, 100 $\mu$M or less, 80 $\mu$M or less, 75 $\mu$M or less, 70 $\mu$M or less, 60 $\mu$M or less, 50 $\mu$M or less, 40 $\mu$M or less, 30 $\mu$M or less, 20 $\mu$M or less, or 10 $\mu$M or less. To repeat, these upper limits can apply to the gallium concentration in the pharmaceutical formulations, or they can apply to the gallium concentration of the gallium solution.

What is provided are compositions, formulations, reagents, salt, optionally in combination with a delivery device such as an inhaler, and methods, for administration to human subjects or patients, to veterinary subjects or pets, to animals used for testing or research, and to agricultural or commercial animals. Moreover, what is provided are reagents, compositions, formulations, and methods, for administration to only human subjects or patients, but not to animals. In another aspect, what is provided are reagents, compositions, formulations, and methods, for treating non-living materials, for example, for treating biological fluids or cells.

In yet another aspect, the invention contemplates a pulmonary drug delivery device, such as an inhaler, wherein the device contains a powdered gallium composition, and wherein the device is capable of delivering the composition to the lungs in a pharmaceutically effective amount. The powdered gallium composition can take the form of a formulation, salt, complex, and the like. Also contemplated is a pulmonary drug delivery device, such as an aerosol inhaler, wherein the device contains a liquid gallium composition, and wherein the device is capable of delivering the liquid composition to the lungs in a pharmaceutically effective amount.

What is provided are compositions, formulations, reagents, salt, optionally in combination with a delivery device such as an inhaler, and methods, that are not capable of enhancing bone repair, of preventing excess loss of calcium from bones, and not capable of facilitating healing or defects of skin.

What is provided is a pharmaceutical formulation comprising gallium, that does not contain maltolate, and/or does not contain isomaltolate. Also, what is provided is a dry powder comprising gallium, that does not contain maltolate, and/or does not contain isomaltolate. Moreover, what is contemplated is a pharmaceutical agent, that does not contain maltolate, or does not contain isomaltolate. In another aspect, what is provided is a solution that does not contain maltolate, and/or does not contain isomaltolate. In yet another embodiment, what is provided is a method of administering a pharmaceutical formulation, a composition, a solution, or an agent, that comprises gallium but does not contain that does not contain maltolate, and/or does not contain isomaltolate.

What is provided is a pharmaceutical formulation, a composition, a pharmaceutical agent, a solution, or a dry powder, that does not contain sucrose, that does not contain trehalose, that does not contain glucose, that does not contain raffinose, that does not contain sorbose, that does not contain melezitose, that does not contain glycerol, that does not contain fructose, that does not contain mannose, that does not contain maltose, that does not contain lactose, that does not contain arabinose, that does not contain xylose, that does not contain ribose, that does not contain rhamnose, that does not contain galactose, that does not contain glycose, that does not contain mannitol, that does not contain xylitol, that does not contain erythritol, that does not contain threitol, that does not contain dextrose, that does not contain fucose, that does not contain polyaspartic acid, that does not contain inositol hexaphosphate, that does not contain sialic acid, that does not contain N-acetylneuraminic acid-lactose, that does not contain sorbitol; that does not contain leucine, that does not contain valine, that does not contain isoleucine, that does not contain tryptophan, that does not contain alanine, that does not contain methionine, that does not contain phenylalanine, that does not contain trileucine, tyrosine, that does not contain histidine, that does not contain proline, that does not contain a tripeptide comprised of two leucines and an amino acid, selected from leucine, valine, isoleucine, tryptophan, alanine, methionine, phenylalanine, tyrosine, histidine, and proline; that does not contain transferrin, that does not contain lactoferrin, that does not contain human serum albumin, that does not contain recombinant human serum albumin; that does not contain citric acid, that does not contain tartaric acid, that does not contain lactic acid; that does not contain a surfactant block co-polymers of polyethylene, polypropylene glycol, polyethylene glycol sorbitan monolaurate, or polyoxyethylenesorbitan monooleate; that does not contain a polysaccharide that is alginic acid, alginates, heparin, heparin sulfates, hyaluronic acid, hyaluronates, chitosan, chitin, starch, starch derivatives, carboxymethyl starch, hydroxyethyl starch, or dextran; that does not contain a polymer that is polyvinyl pyrrolidone (PVP), gelatin, collagen, chrondroitin sulfate, or polyvinyl alcohol.

The present invention, in some aspects, provides compositions and methods that reduce, avoid, or prevent, the development of insoluble protein in the lungs, or in another compartment or tissue in the body. By reducing, avoiding, or preventing the development of insoluble protein, the present invention (in at least some embodiments) can reduce, avoid, or prevent, the development of inflammation, pathology, or injury resulting from the insoluble protein.

When particles enter the lungs, they engulfed by alveolar macrophages, and result in a pathological response that leads to lung injury, or result in carriage to the pharynx and then swallowed (Brain, J. D. (1980) Environ. Health Perspectives 35:21-28; Edwards, D. A., Dunbar, C. (2002) Annu Rev. Biomed. Eng. 4:93-107). An account of the pathological effects of insoluble protein to the lung is available from studies of lung injury resulting from entry of meconium into the lungs. Meconium comprises insoluble protein (Herlant-Peers, M. C., et al. (1981) Eur J. Biochem. 117:291-300). Exposure of meconium to lungs occurs naturally. When meconium enters the lungs, the result can include inflammation, increases in macrophages, increases in neutrophils, and pathological effects similar to those found with asthma (Mokra, D., et al. (2007) J. Physiol. Pharmacol. 58:Suppl. 5:399-407).

Anti-microbial properties of the present invention can be determined as follows. What can be determined includes anti-microbially effective concentrations, anti-microbially effective molar ratios of gallium and citrate, anti-microbially effective molar ratios of gallium and an anion or complexing agent, and anti-microbially effective routes of administration. These parameters can be determined, for example, by measuring the killing of the microbe in question, loss of titer of the microbe, inhibition of growth of the microbe, impairment of some aspect of the metabolism of the microbe, or impairment of iron transport of the microbe. Also, these parameters can be measured by assessing increased immune response against the microbe in question, e.g., increased response by antibodies, dendritic cells, or T cells. These parameters can be measured, e.g., using agar medium plates, using agar medium in a culture tube, using an aerobic, microaerobic, or anaerobic liquid culture medium, using an animal model, or using human subjects.

Risk for infections can be determined, for example, by methods disclosed by Lange (2009) Pneumonol Alergol Pol. 77 (3):284-288; Amano (2006) Intern. Med. 45:991-992; Duncan and Wilkes (2005) Proc. Am. Thorac. Soc. 2:449-455; West, et al. (2002) J. Am. Med. Assoc. 287:2958-2967.

Aerosols, propellants, inhalers, methods for deriving a dry powder from a solution, relevant formulations, are available. See, e.g., Hickey, A. J. (2003) Pharmaceutical Inhalation Aerosol Technology, 2nd ed., (Drugs and the Pharmaceutical Sciences) Informa Healthcare; Zeng, X. M., Martin, G. P., Marriott, C. (2000) Particulate Interactions in Dry Powder Formulation for Inhalation (Pharmaceutical Science Series) Informa Healthcare; and Gradon, L., Marijnissen, J. C. (2003) Optimization of Aerosol Drug Delivery, Springer.

EXAMPLES

The following examples are offered to illustrate, but not to limit the scope of the claimed invention.

Example 1

Solubility of Gallium in Citrate Solution

The solubility of gallium in human blood plasma was determined by varying the citrate concentration in gallium-citrate compositions. Gallium-citrate compositions were prepared at either 1:1 or 2:1 sodium citrate-to-gallium nitrate molar ratios. The concentration of gallium nitrate was 72 mM. 20 microliters of the 0.22 µm-filtered gallium-citrate compositions were added to 200 microliters of human plasma and were photographed immediately (FIG. 1). The 1:1 citrate-to-gallium solution resulted in precipitation upon addition to human blood plasma (FIG. 1, right image), while the addition of 2:1 citrate-to-gallium solution exhibited no observable precipitation (FIG. 1, left image).

Plasma was prepared as follows. Freshly collected blood in heparinized tubes was layered on top of Mono-Poly® Resolving medium (e.g., Fisher Scientific) (20 ml medium, 25 ml blood). Tubes were then centrifuged at 350 g for 30 min. The top layer is the plasma. The experiment was conducted at room temperature (about 22° C.) and the precipitate was observed immediately upon the addition of gallium-citrate to plasma.

Trileucine (tri-leucine) has been described (see, e.g., Lechuga-Ballesteros, D., et al. (2008) J. Pharm. Sci. 97:287-302.

What is also provided is a method for assessing solubility of gallium as a salt or complex, using other biological fluids, including lymph, interstitial fluid, or serum. These fluids can be prepared in the presence or absence of heparin. In one non-limiting example, gallium-citrate compositions can be prepared, using sodium citrate and gallium nitrate, where the molar ratios of citrate:gallium are 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.5:1, 3:1, 3.5:1, 4:1, and the like. In a preferred aspect, the concentration of gallium is 72 mM. 20 microliters of the gallium-salt composition, e.g., gallium citrate, can be added to 200 microliters of a biological fluid, e.g., pulmonary lymph, at room temperature, photographed immediately, and assessed for turbidity.

Regarding formulations of gallium citrate, what is provided is gallium citrate at a molar citrate:gallium molar ratio of less than 20:1, less than 15:1, less than 10:1, less than 8:1, less than 6:1, less than 5:1, less than 4:1, less than 3.8:1, less than 3.6:1, less than 3.5:1, less than 3.4:1, less than 3.3:1, less than 3.2:1, less than 3.1:1, less than 3.0:1, less than 2.9:1, less than 2.8:1, less than 2.7:1, less than 2.6:1, less than 2.5:1, less than 2.4:1, less than 2.3:1, less than 2.2:1, less than 2.1:1, less than 2.0:1, and so on. It will be appreciated that, with respect to citrate in these molar ratios, a reduced proportion of citrate can result in a more concentrated active substance, and a more effective drug. The therapeutic efficacy of the formulation or solution of the present invention, in some aspects, may improve by using a molar ratio of citrate:gallium that is less than 20:1, less than 15:1, less than 10:1, less than 8:1, less than 6:1, less than 5:1, less than 4:1, and so on.

The following concerns formulations, compositions, salts, agents, solutions, aerosols, dry powders, inhalers, and related methods, that have reduced amounts of nitrate. The invention, in some embodiments, provides a pharmaceutical formulation wherein the molar ratio of nitrate:gallium is lower than 1.0:1.0, lower than 0.8:1.0, lower than 0.5:1.0, lower than 0.4:1.0, lower than 0.3:1.0, lower than 0.2:1.0, lower than 0.1:1.0, lower than 0.05:1.0, lower than 0.01:1.0, and so on. In another aspect, what is provided is a solution, an aerosol, a pharmaceutical agent, a dry powder, a particle having a mean diameter under 10 micrometers, and the like, wherein the molar ratio of nitrate:gallium is lower than 1.0:1.0, lower than 0.8:1.0, lower than 0.5:1.0, lower than 0.4:1.0, lower than 0.3:1.0, lower than 0.2:1.0, lower than 0.1:1.0, lower than 0.05:1.0, lower than 0.01:1.0, and so on.

Example 2

Effect of Gallium-Citrate Concentration on Aerosol Droplet Diameter

Figure 2:
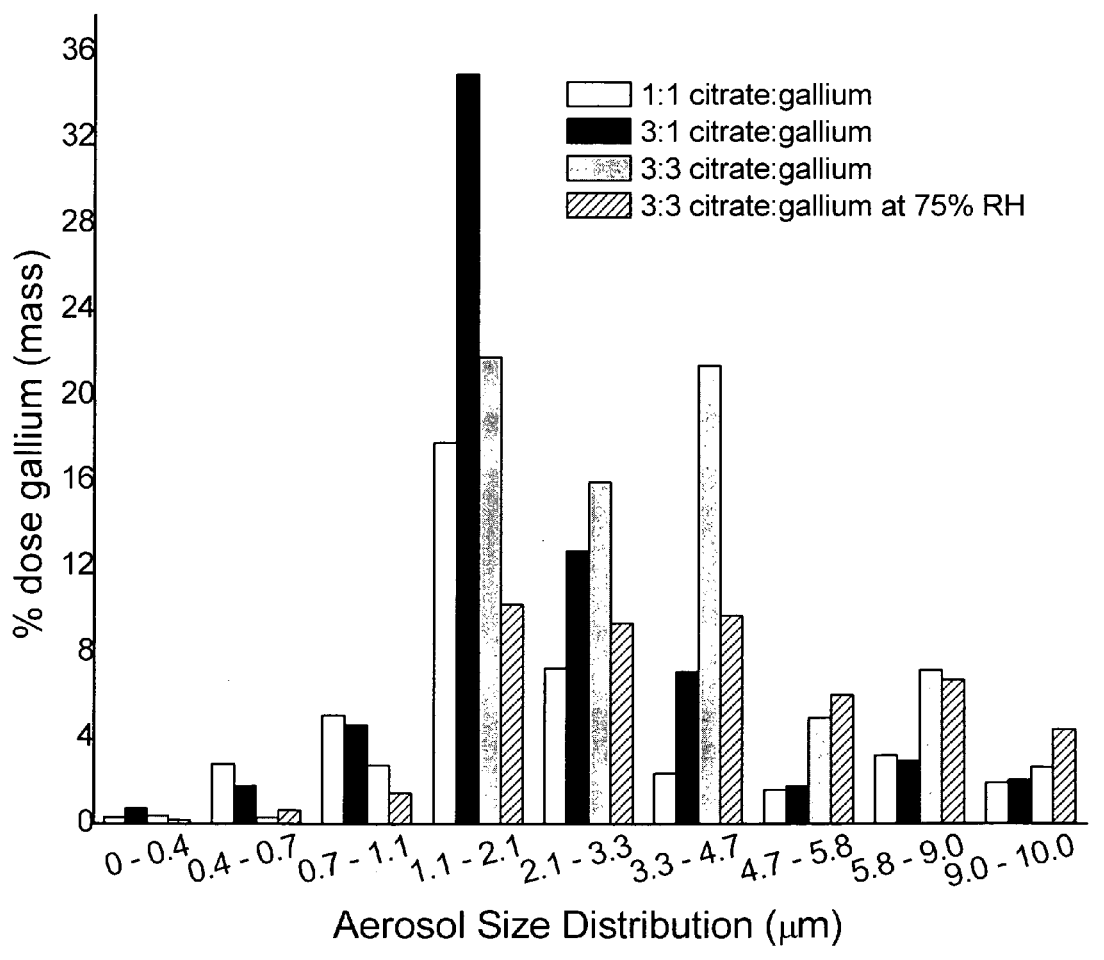

Gallium nitrate-sodium citrate compositions comprised of concentrations shown in Table 1 were prepared. All solutions were adjusted to pH 6.8. The aerosol droplet size distribution was determined by aerosolizing the gallium-citrate compositions using Evo Aeroneb Go micropump nebulizer into an Andersen Cascade Impactor (ACI) unit. The nebulizer was held close to the ACI inlet until no aerosol was visible. The flow rate of the ACI was set to 28 LPM and was operated under ambient condition unless otherwise noted. When the nebulizer reservoir had been emptied, the gallium concentration on each of the ACI stages was analyzed using Perkin Elmer 4100ZL atomic absorption spectrophotometer equipped with a gallium lamp. The ACI plates were rinsed and then soaked with 1% $HNO_3$. The dissolved gallium solution was diluted further with 1% $HNO_3$ to appropriate concentrations prior to analysis. Nebulizer run time and mass median aerodynamic diameter (MMAD) for the tested solutions are shown in Table 1. The droplet size distribution of the test solutions are shown in FIG. 2.

TABLE 1

| Humidity | Gallium Concentration (mM) | Citrate Concentration (mM) | Nebulizer run time (min) | MMAD (μm) |
|---|---|---|---|---|
| Ambient | 98 | 98 | 3.00 | 1.8 |
| Ambient | 98 | 293 | 3.75 | 1.9 |
| 75% RH | 98 | 293 | 3.25 | 3.6 |
| Ambient | 293 | 880 | 9.08 | 3.1 |

Example 3

Preparation of Dry Powder Gallium Using Spray Drying Method $Ga(NO_3)_3 \cdot 9H_2O$ was dissolved in nano-pure water to obtain 2.6% (w/v) $Ga(NO_3)_3$. The solution was spray dried at $T_{in}/T_{out}$=80/60° C., q=0.5 mL/min, and $P_{atm}$=15 psi. The powder was collected under controlled temperature and humidity of 30° C. and <5% RH, respectively. The residual moisture content was 27.8% (w/w). 50 mg of the powder was encapsulated inside of a type 2 capsule and tested for particle size distribution using an Andersen cascade impactor (ACI) fitted with Turbospin® (PH & T, Milan, Italy) under a flow rate of 28 L/min. $FPD_{<3.3 \mu m}$ and $FPD_{<4.7 \mu m}$ were 27% and 39%, respectively. The MMAD was 5.3 μm and the ED was determined to be 54.5%.

FPD is fine particle distribution. For example, an FPD<4.7 um indicates how much of the deposited powder is less than 4.7 microns in size. In a preferred embodiment, FPD<4.7 um is a minimum, because it provides that the powder is able to flow aerodynamically deep into the lung, where there are more alveoli to absorb the gallium. Moreover, the further the powder flows into the lung, the more effective the gallium will likely be to kill the bacteria in the lung.

Figure 3:
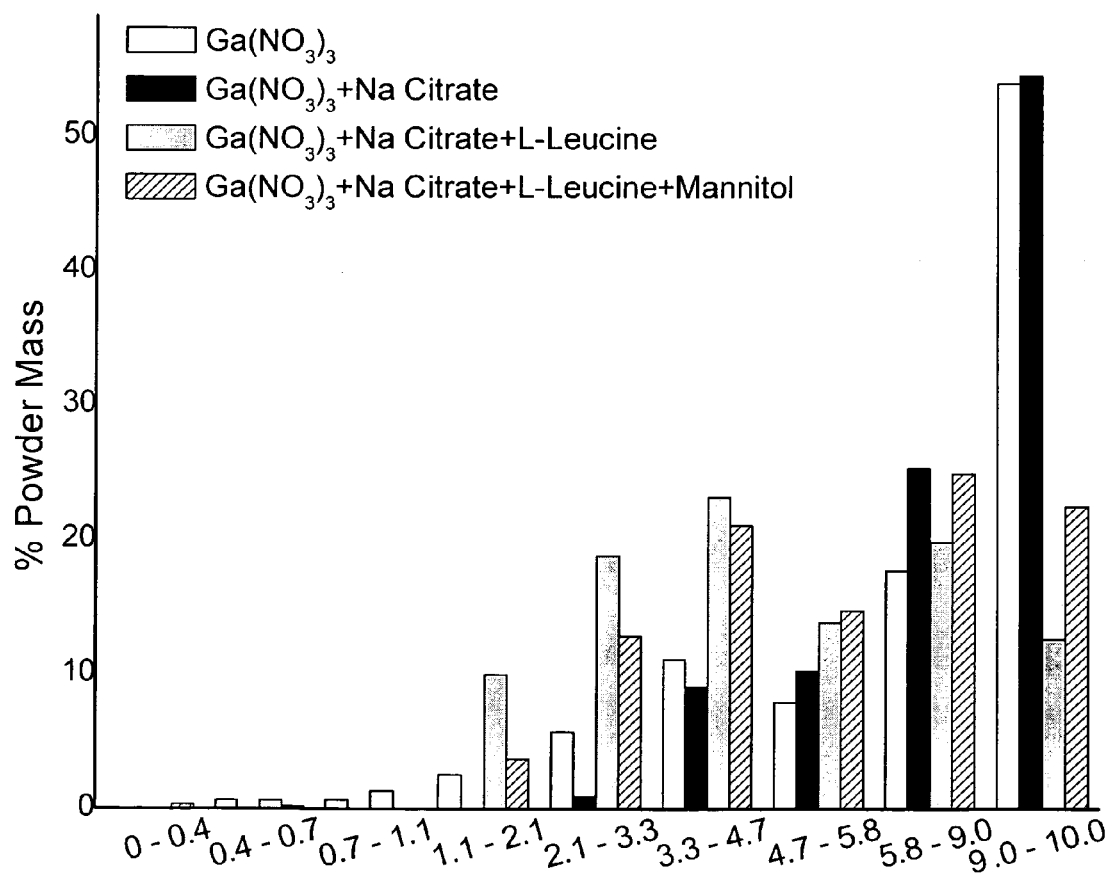
Figure 4:
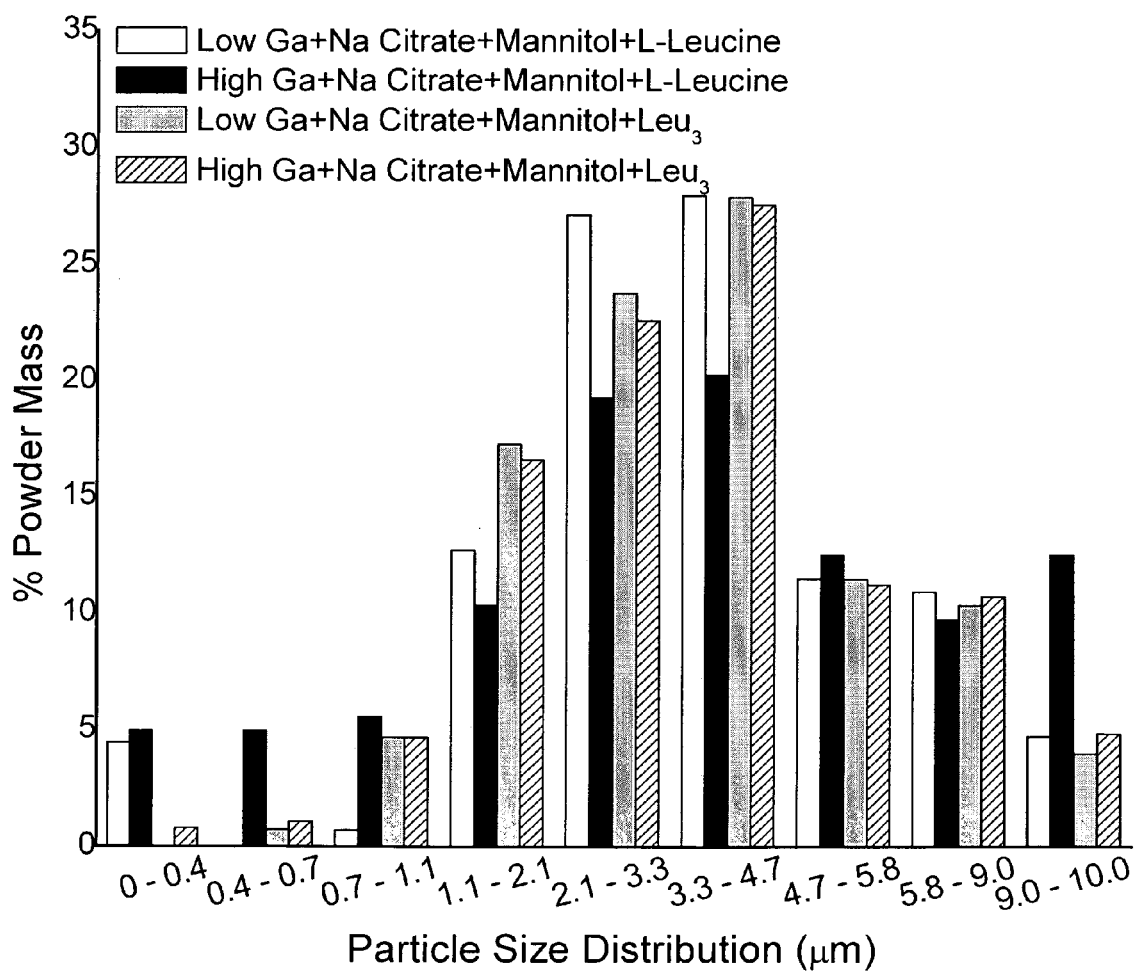

Gallium-containing compositions prepared with other suitable excipients were prepared and spray dried under the same conditions. The compositions of these gallium formulations are shown in Table 2. All of the solutions were prepared at pH7.0 except those containing tri-leucine, which were prepared at pH 8.0. The results of the aerosol testing as well as the residual moisture contents are shown in Table 3. The effect of L-leucine and tri-leucine on the particle size distribution is shown in FIGS. 3 and 4. The compositions shown in Table 2 were mixed in aqueous solution and then were prepared into a dry powder by spray drying, using the conditions stipulated in Example 3. The aerosol properties in Table 3 were then obtained from ACI analyses.

TABLE 2

| Formulation # | Gallium $NO_3$ (%, w/v) | Na Citrate (%, w/v) | Mannitol (%, w/v) | L-leucine (%, w/v) | Tri-leucine (%, w/v) |
|---|---|---|---|---|---|
| 1 | 1.6 | 1.6 | | | |
| 2 | 1.6 | 1.1 | 0.6 | | |
| 3 | 1.5 | 1.0 | 0.6 | | 0.2 |
| 4 | 1.5 | 1.0 | 0.6 | 0.8 | |
| 5 | 1.5 | 1.0 | 0.6 | 1.7 | |
| 6 | 1.5 | 1.0 | 0.6 | 0.4 | |
| 7 | 1.5 | 1.0 | | 1.7 | |
| 8 | 1.5 | | 0.6 | 1.7 | |
| 9 | 1.5 | | 0.6 | 0.4 | |
| 10 | 1.5 | | 1.5 | | |
| 11 | 0.4 | 1.1 | 0.6 | 1.8 | |
| 12 | 0.4 | 1.1 | 0.6 | 0.5 | |
| 13 | 1.5 | 1.0 | 0.6 | | 0.4 |
| 14 | 0.4 | 1.1 | 0.6 | | 0.5 |
| 15 | 1.5 | | | 1.7 | |
| 16 | 1.5 | | | 0.4 | |
| 17 | 0.4 | | | 1.9 | |
| 18 | 1.5 | 1.0 | | 0.4 | |
| 19 | 1.5 | 1.0 | 0.6 | 0.2 | |
| 20 | 1.5 | 1.0 | 0.6 | 0.1 | |
| 21 | 1.5 | 1.0 | | 0.4 | |
| 22 | 1.5 | 1.5 | 0.6 | 0.4 | |
| 23 | 1.5 | 1.5 | | 0.4 | |

TABLE 3

| Formulation # | Residual Moisture (%, w/w) | $FPD_{<3.3 \mu m}$ (%) | $FPD_{<4.7 \mu m}$ (%) | MMAD (μm) | ED (%) |
|---|---|---|---|---|---|
| 1 | 7.7 | 1 | 10 | >6 | 34.0 |
| 2 | 8.3 | 6 | 17 | >6 | 41.0 |
| 3 | 3.5 | 41 | 66 | 3.5 | 63.3 |
| 4 | 5.3 | 32 | 60 | 4.1 | 52.3 |
| 5 | 3.5 | 45 | 67 | 3.3 | 72.2 |
| 6 | 5.1 | 40 | 60 | 3.6 | 57.1 |
| 7 | 4.0 | 40 | 66 | 3.7 | 72.2 |
| 8 | 6.0 | 44 | 71 | 3.5 | 58.2 |
| 9 | 10.0 | 49 | 74 | 3.3 | 44.1 |
| 10 | 2.2 | 47 | 72 | 3.5 | 64.7 |
| 11 | 2.2 | 47 | 72 | 3.3 | 63.5 |
| 12 | 2.4 | 41 | 68 | 3.5 | 64.7 |
| 13 | 6.7 | 45 | 72 | 3.5 | 70.2 |
| 14 | 3.5 | 46 | 74 | 3.4 | 67.4 |
| 15 | 6.4 | 46 | 73 | 3.5 | 64.0 |
| 16 | 18 | 49 | 75 | 3.3 | 49.7 |
| 17 | 1.6 | 56 | 82 | 2.9 | 71.0 |
| 18 | 7.4 | 29 | 55 | 4.4 | 47.0 |
| 19 | 5.6 | 25 | 49 | 4.8 | 52.2 |
| 20 | 7.0 | 12 | 26 | >6 | 50.7 |
| 21 | 6.9 | 17 | 42 | 5.3 | 45.6 |
| 22 | 5.8 | 17 | 38 | 5.6 | 58.2 |
| 23 | 5.5 | 31 | 54 | 4.4 | 61.2 |

Example 4

Preparation of Dry Powder Gallium Using Spray Drying Method

Ga(NO$_3$)$_3$·9H$_2$O was dissolved in nano-pure water to obtain 1.5% (w/v) Ga(NO$_3$)$_3$. To the solution, 0.6% (w/v) mannitol and 0.4% (w/v) L-leucine were added and the pH was adjusted to pH 7.0. The mixture was spray-dried at $T_{in}/T_{out}$=80/60° C., q=0.5 mL/min, and $P_{atm}$=24 psi. The powder was collected under controlled temperature and humidity of 30° C. and <5% RH, respectively. The residual moisture content was 7.5% (w/w). 50 mg of the powder was encapsulated inside of a type 2 capsule and tested for particle size distribution using an Andersen cascade impactor (ACI) fitted with Turbospin® under a flow rate of 28 L/min. FPD$_{<3.3\mu m}$ and FPD$_{<4.7\mu m}$ were 65% and 80%, respectively. The MMAD was 2.6 μm and the ED was determined to be 43.1%.

Example 5

Preparation of Dry Powder Gallium Using Spray Drying Method

Ga(NO$_3$)$_3$·9H$_2$O was dissolved in nano-pure water to obtain 1.5% (w/v) Ga(NO$_3$)$_3$. To the solution, 0.6% (w/v) mannitol and 0.4% (w/v) L-leucine were added and the pH was adjusted to pH 7.0. The mixture was spray-dried at $T_{in}/T_{out}$=120/80° C., q=0.5 mL/min, and $P_{atm}$=30 psi. The powder was collected under controlled temperature and humidity of 30° C. and <5% RH, respectively. The residual moisture content was 5.7% (w/w). 50 mg of the powder was encapsulated inside of a type 2 capsule and tested for particle size distribution using an Andersen cascade impactor (ACI) fitted with Turbospin® under a flow rate of 28 L/min. FPD$_{<3.3\mu m}$ and FPD$_{<4.7\mu m}$ were 17% and 20%, respectively. The MMAD was >6 μm and the ED was determined to be 27.3%.

Example 6

Preparation of Dry Powder Gallium Using Spray Drying Method

Sodium citrate dihydrate was dissolved in nano-pure water to obtain 1.0% (w/v) sodium citrate. To the solution, 0.6% (w/v) and 0.4% (w/v) mannitol and L-leucine, respectively, were added and Ga(NO$_3$)$_3$·9H$_2$O was dissolved to obtain 1.5% (w/v) Ga(NO$_3$)$_3$. The mixture was spray-dried at $T_{in}/T_{out}$=150/100° C., q=0.5 mL/min, and $P_{atm}$=34 psi. The powder was collected under controlled temperature and humidity of 30° C. and <5% RH, respectively. The residual moisture content was 3.7% (w/w). 50 mg of the powder was encapsulated inside of a type 2 capsule and tested for particle size distribution using an Andersen cascade impactor (ACI) fitted with Turbospin® under a flow rate of 28 L/min. FPD$_{<3.3\mu m}$ and FPD$_{<4.7\mu m}$ were 9% and 11%, respectively. The MMAD was >6 μm and the ED was determined to be 33.6%. Gallium-containing compositions prepared with other suitable excipients were prepared and spray dried under the same conditions. The compositions of these gallium formulations are shown in Table 4. All of the solutions were prepared at pH 7.0. The results of the aerosol testing as well as the residual moisture contents are shown in Table 5.

TABLE 4

| Formulation # | Gallium NO$_3$ (%, w/v) | Na Citrate (%, w/v) | Mannitol (%, w/v) | L-leucine (%, w/v) |
|---|---|---|---|---|
| 24 | 1.5 | | | 0.4 |
| 25 | 0.4 | 1.1 | 0.6 | 0.5 |
| 26 | 1.5 | 1.0 | | 0.4 |

TABLE 5

| Formulation # | Residual Moisture (%, w/w) | FPD$_{<3.3\mu m}$ (%) | FPD$_{<4.7\mu m}$ (%) | MMAD (μm) | ED (%) |
|---|---|---|---|---|---|
| 24 | 16.2 | 33 | 39 | >6 | 24.2 |
| 25 | 2.3 | 55 | 74 | 3.0 | 59.5 |
| 26 | 4.9 | 20 | 24 | >6 | 36.3 |

Example 7

Preparation of Dry Powder Gallium Using Spray Drying Method

Ga(NO$_3$)$_3$·9H$_2$O was dissolved in nano-pure water to obtain 2.6% (w/v) Ga(NO$_3$)$_3$. The solution was spray dried at $T_{in}/T_{out}$=55/35° C., q=0.5 mL/min, and $P_{atm}$=34 psi. The powder was collected under controlled temperature and humidity of 30° C. and <5% RH, respectively. The residual moisture content was 31.7% (w/w). 50 mg of the powder was encapsulated inside of a type 2 capsule and tested for particle size distribution using an Andersen cascade impactor (ACI) fitted with Turbospin® under a flow rate of 28 L/min. FPD$_{<3.3\mu m}$ and FPD$_{<4.7\mu m}$ were 4% and 10%, respectively. The MMAD was >6 μm and the ED was determined to be 36.6%.

Example 8

Preparation of Dry Powder Gallium Using Spray Drying Method

Ga(NO$_3$)$_3$·9H$_2$O was dissolved in nano-pure water to obtain 1.5% (w/v) Ga(NO$_3$)$_3$. To the solution, 0.4% (w/v) Iso-leucine was added. The mixture was spray-dried at $T_{in}/T_{out}$=80/60° C., q=0.5 mL/min, and $P_{atm}$=15 psi. The powder was collected under controlled temperature and humidity of 30° C. and <5% RH, respectively. The residual moisture content was 18.3% (w/w).

Gallium-containing compositions prepared with other suitable excipients were prepared and spray dried under the same conditions. The compositions of these gallium formulations are shown in Table 6 along with their residual moisture contents.

TABLE 6

| Formulation # | Gallium NO$_3$ (%, w/v) | Na Citrate (%, w/v) | Mannitol (%, w/v) | Iso-leucine (%, w/v) | D-leucine (%, w/v) | Residual Moisture (%, w/w) |
|---|---|---|---|---|---|---|
| 27 | 1.5 | 1.5 | 0.6 | 0.4 | | 4.7 |
| 28 | 1.5 | | | | 0.4 | 20.0 |
| 29 | 1.5 | 1.5 | 0.6 | | 0.4 | 5.4 |

Example 9

Preparation of Dry Powder Gallium Using Spray Drying Method

Sodium citrate dihydrate was dissolved in nano-pure water to obtain 2.8% (w/v) sodium citrate. Ga(NO$_3$)$_3$.9H$_2$O was added to the solution to obtain 2.8% (w/v) Ga(NO$_3$)$_3$. To the gallium-containing solution, ethanol was added to give a final composition of 10% (v/v). The mixture was spray-dried at $T_{in}/T_{out}$=80/60° C., q=0.5 mL/min, and $P_{atm}$=15 psi. The powder was collected under controlled temperature and humidity of 30° C. and <5% RH, respectively. The residual moisture content was 6.3% (w/w).

Gallium-containing compositions prepared with other suitable excipients containing ethanol were prepared and spray dried under the same conditions. The compositions of these gallium formulations are shown in Table 7 along with their residual moisture contents.

TABLE 7

| Formulation # | Gallium NO$_3$ (%, w/v) | Na Citrate (%, w/v) | Mannitol (%, w/v) | L-leucine (%, w/v) | EtOH (%, v/v) | Residual Moisture (%, w/w) |
|---|---|---|---|---|---|---|
| 30 | 2.8 | 2.8 | | | 30 | 7.7 |
| 31 | 2.8 | 2.8 | | | 50 | 10.3 |
| 32 | 1.6 | 1.6 | | 0.4 | 10 | 8.5 |
| 33 | 1.6 | 1.6 | | 0.4 | 30 | 9.1 |
| 34 | 1.6 | 1.6 | | 0.4 | 50 | 7.3 |
| 35 | 1.4 | 1.4 | 0.02 | 0.4 | 10 | 6.6 |
| 36 | 1.4 | 1.4 | 0.02 | 0.4 | 30 | 6.9 |
| 37 | 1.4 | 1.4 | 0.02 | 0.4 | 50 | 6.7 |
| 38 | 1.4 | 1.4 | 0.09 | 0.4 | 10 | 7.8 |
| 39 | 1.4 | 1.4 | 0.09 | 0.4 | 30 | 7.7 |
| 40 | 1.4 | 1.4 | 0.09 | 0.4 | 50 | 8.5 |
| 41 | 1.3 | 1.3 | 0.6 | 0.4 | 10 | 5.1 |
| 42 | 1.3 | 1.3 | 0.6 | 0.4 | 50 | 5.7 |

TABLE 8

| Formulation # | %, w/v | | | | % Moisture | Crystalline/ Amorphous |
|---|---|---|---|---|---|---|
| | GaNO$_3$ | Na Citrate | Mannitol | L-leucine | | |
| neat | 2.6 | | | | 31.7 | Amorphous |
| 1 | 1.6 | 1.6 | | | 7.7 | Crystalline |
| 2 | 1.5 | 1.1 | 0.6 | | 8.3 | Crystalline |
| 6 | 1.5 | 1.0 | 0.6 | 0.4 | 5.6 | Crystalline |
| 10 | 1.5 | | 1.5 | | 4.8 | Amorphous |
| 16 | 1.5 | | | 0.4 | 20.1 | Amorphous |
| 23 | 1.5 | 1.5 | | 0.4 | 5.5 | Amorphous |

Example 10

Characterization of Spray Dried Gallium Composition

Figure 5:
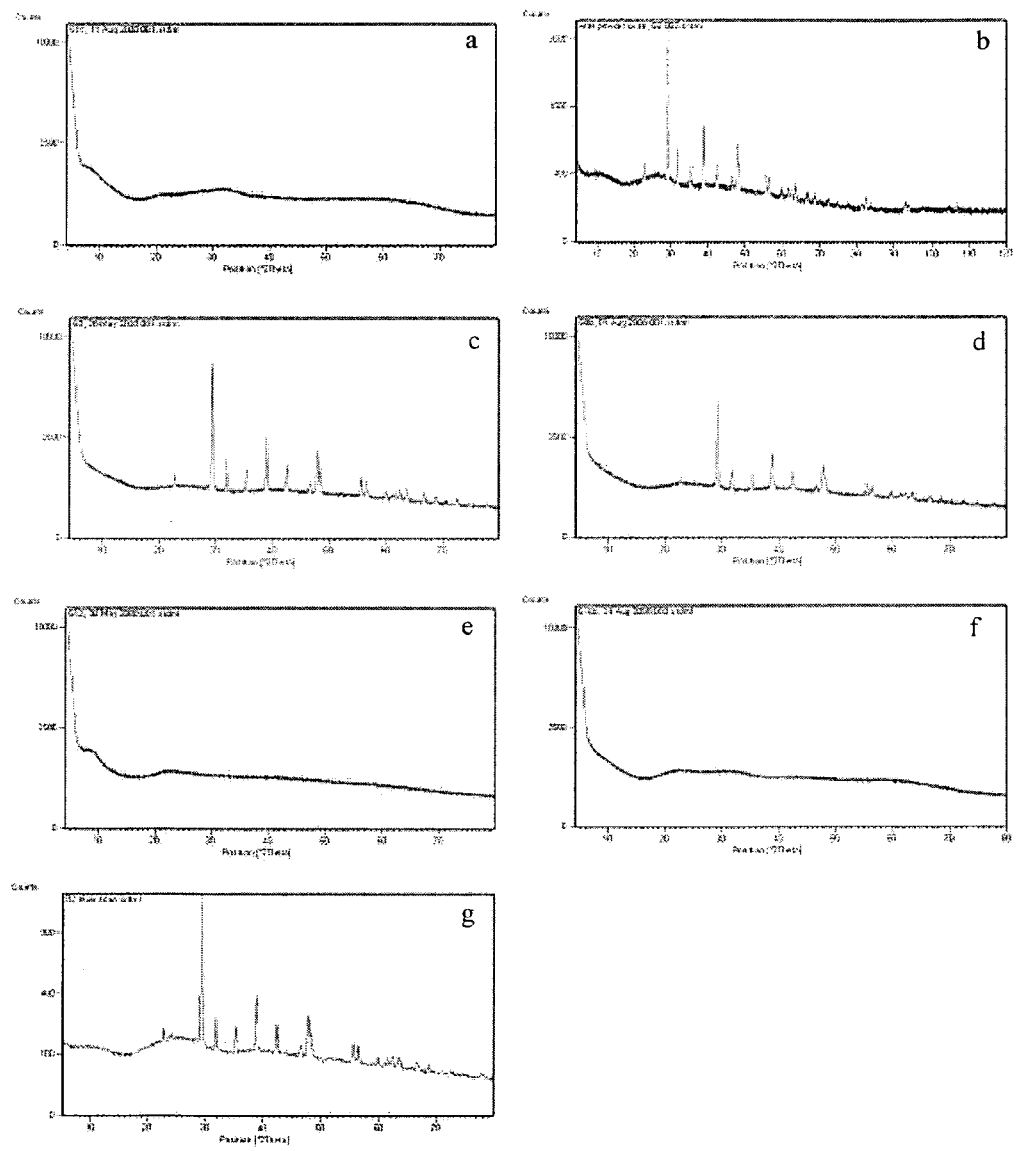

Crystallinity of the spray dried gallium powders was determined using a Philips X-Pert Pro MPD powder diffractometer. The radiation used was generated by a Cu Kα source with a wavelength of 1.5406 Å at 45 kV and 40 mA. Samples were scanned from 5° to 75° 2θ at a scanning rate of 1.2° 2θ/min using a slit width of 0.25°. Particular emphasis was placed on determining the effects of the various excipients on the crystallinity of the spray dried particles. The composition of the gallium formulations examined, as well as the residual moisture content and a qualitative analysis of crystallinity are shown in Table 8. X-ray diffractometer (XRD) scans reveal that spray dried gallium nitrate is amorphous as are mannitol and L-leucine (FIG. 5). Sodium citrate, however, is crystalline and the crystallinity is maintained even in the presence of other excipients.

Example 10

Characterization of Spray Dried Gallium Composition

Figure 6A:
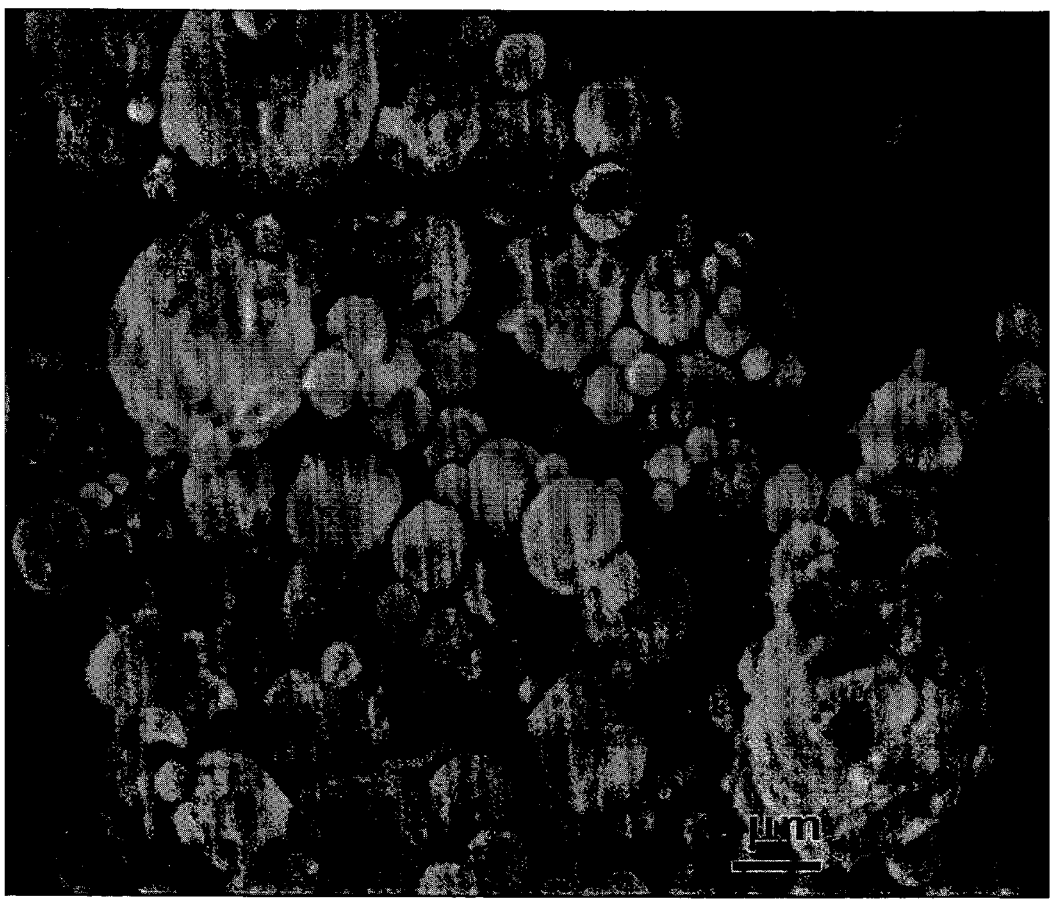
FIG. 6 shows the SEM images of spray dried gallium preparations. Spray dried neat gallium nitrate (a), gallium nitrate with sodium citrate (b); gallium nitrate with sodium citrate and L-leucine (c); gallium nitrate with mannitol and L-leucine (d); and gallium nitrate with sodium citrate, mannitol, and L-leucine (e).

Particle morphology of the spray dried gallium powders was examined by scanning electron microscopy (SEM). SEM imaging was conducted with JEOL JSM-6700F cold cathode field emission SEM. Typically, the powders were affixed to a double-sided carbon tape atop an aluminum stub, and sputter-coated with platinum for 100 sec. The instrument used for platinum coating was Polaron Range SC7640 High Resolution Sputter Coater from Quorum Technologies (UK). Coating was conducted twice with a 5 minute rest period in between the runs to avoid over heating the sample. The approximate thickness of the platinum coating is 15 nm. Several gallium powders, of varying composition, were imaged immediately after spray drying. Imaging revealed that spray drying gallium nitrate resulted in spherical particles (FIG. 6a), in contrast to freeze dried gallium nitrate, which maintained the cubic morphology of the neat material.

Figure 6B:
Figure 6C:
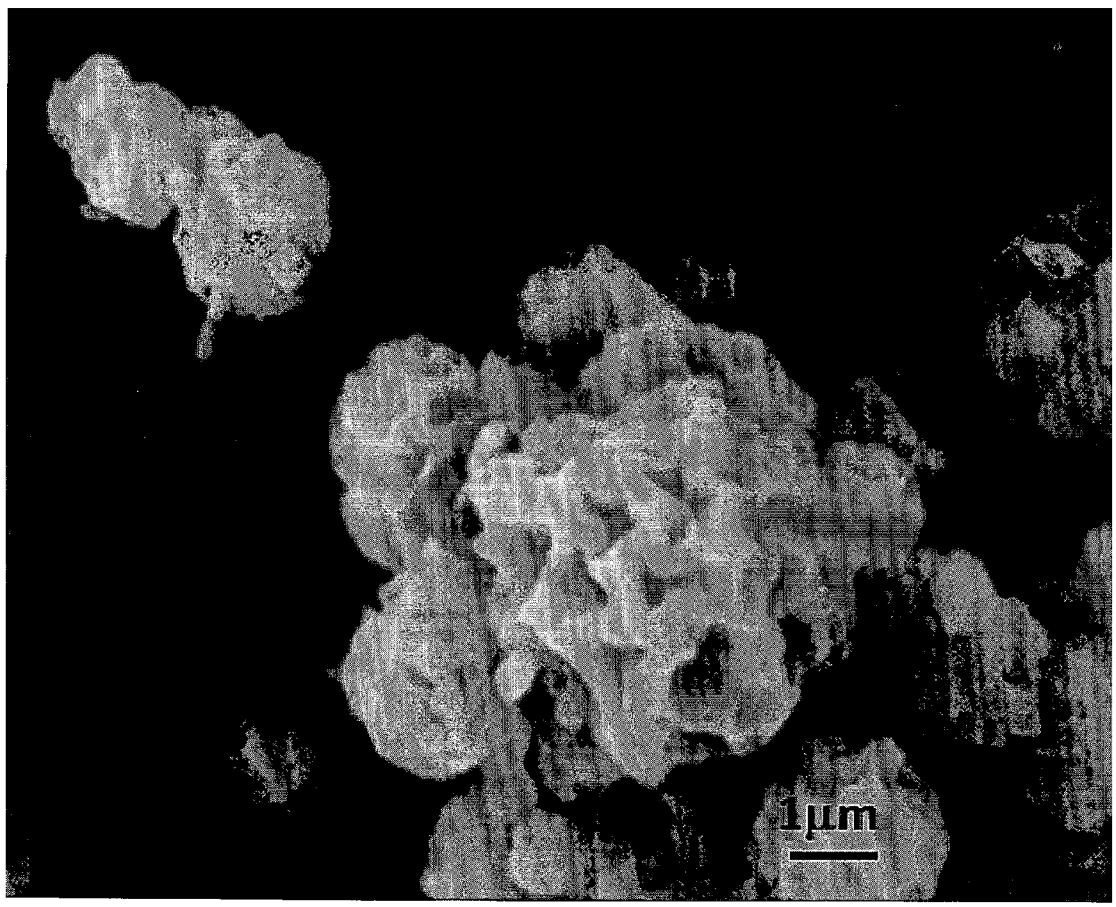
Figure 6D:
Figure 6E:
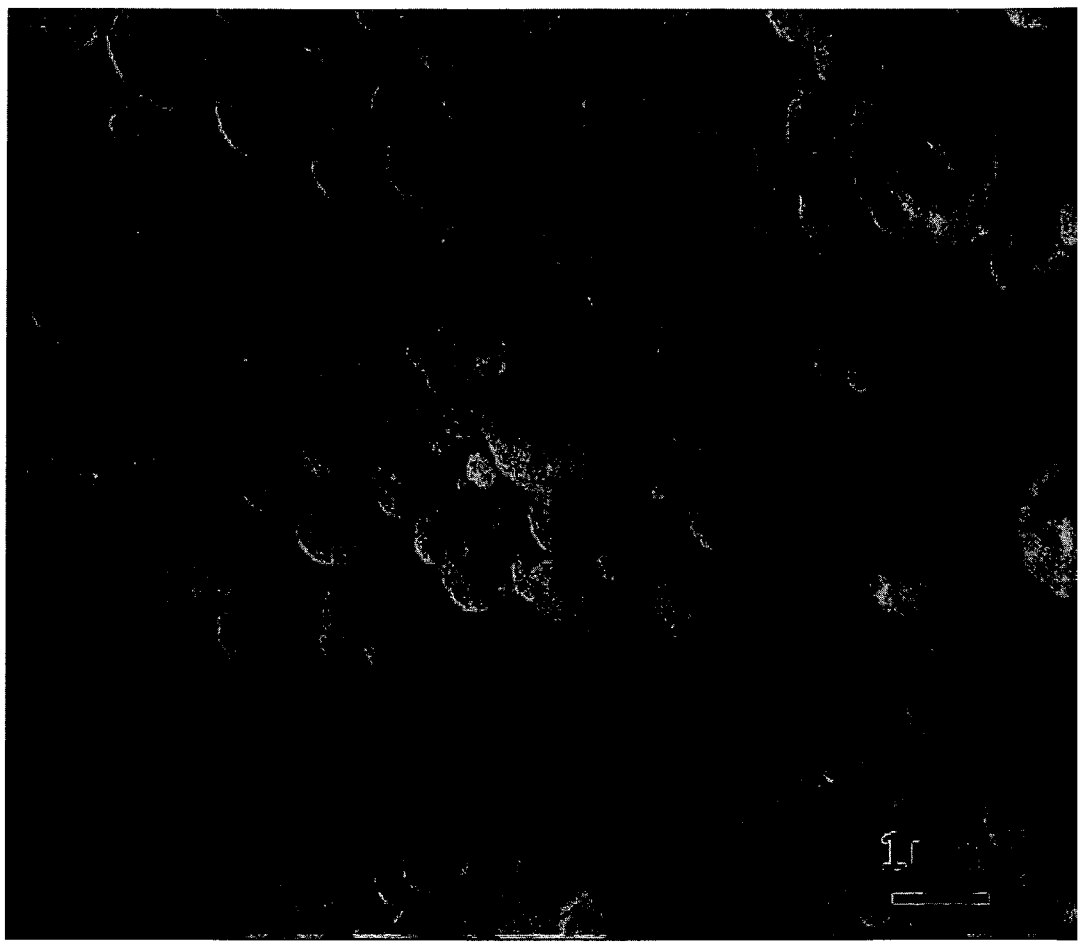

Spray drying a gallium composition, containing gallium nitrate and sodium citrate at 1:1 molar ratio, resulted in spherical particles with cubical structures enriched on the particle surface (FIG. 6b), while those containing L-leucine resulted in spherical particles with wrinkled morphologies (FIGS. 6c, d and e).

Example 11A

In Vivo Effect of Gallium

In order to compare the pharmacokinetics of intratracheally administered gallium, two gallium-containing compositions were prepared, as shown in Table 9. One placebo formulation was also prepared. These solutions were administered intratracheally to female Sprague Dawley rats weighing approximately 200 g. The rats were anesthetized with 1-3% Isoflurane via inhalation and the gallium-containing compositions were administered using a syringe. The blunt tip of the feeding needle was inserted down the oral cavity into the trachea to the level of bifurcation and 200 µL of the solution was administered. Upon completion of intratracheal instillation, the animals were allowed to recover. The animals were sacrificed at various time points (0 h, 1 h, 3 h, 6 h, 24 h, and 72 h) and their kidneys, stomach, liver and lungs were collected in addition to the lung lavage fluid and blood. As control, formulation #45 was administered intravenously as well.

TABLE 9

| Formulation # | Gallium NO$_3$ (%, w/v) | Gallium PPX (%, w/v) | Na Citrate (%, w/v) | Mannitol (%, w/v) |
|---|---|---|---|---|
| 43 | 0.74 | | 0.74 | 1.0 |
| 44 | | 0.05 | 0.74 | 1.0 |
| 45 | | | 0.74 | 1.0 |

Gallium PPX stands for Gallium Protoporphyrin. The pH of gallium PPX-containing solution was adjusted to 7.8, while the other two were adjusted to 7.0. All solutions were filtered twice through 0.22 µm filter.

Example 11B

In Vivo Effect of Gallium

In order to determine the toxicity of intratracheally administered gallium, several gallium-containing compositions were prepared, as shown in Table 10. Two placebo formulations, formulation 51 and 52, were also prepared. For the two formulations containing L-leucine, the solutions were spray dried at $T_{in}/T_{out}$=80/60° C., q=0.5 mL/min, and $P_{atm}$=15 psi. The powder was collected under controlled temperature and humidity of 30° C. and <5% RH, respectively. The residual moisture content was 5.0% (w/w) for both powders. Prior to administration, the spray dried powders were rehydrated to match the initial citrate concentration prior to spray drying, i.e. 14.7% (w/v). All of the solutions listed in Table 10 were administered intratracheally to female Sprague Dawley rats weighing approximately 200 g. The rats were anesthetized with 1-3% Isoflurane via inhalation and the gallium-containing compositions were administered using a syringe. The blunt tip of the feeding needle was inserted down the oral cavity into the trachea to the level of bifurcation and 50 µL of the solution was administered. Upon completion of intratracheal instillation, the animals were allowed to recover. The animals were dosed once daily for the next 13 days and sacrificed on the 14$^{th}$ day. Their kidneys, stomach, liver and lungs were collected in addition to the lung lavage fluid and blood.

TABLE 10

| Formulation # | Gallium NO$_3$ (%, w/v) | Gallium PPX (%, w/v) | Na Citrate (%, w/v) | Mannitol (%, w/v) | L-leucine (%, w/v) |
|---|---|---|---|---|---|
| 46 | 14.7 | | 14.7 | 1.0 | |
| 47 | 14.7 | | 14.7 | 0.6 | 0.9 |
| 48 | | 0.05 | 0.74 | 1.0 | |
| 49 | | | 14.7 | 1.0 | |
| 50 | | | 14.7 | 0.6 | 0.9 |

Gallium PPX stands for Gallium Protoporphyrin. The pH of the gallium NO$_3$ solutions were adjusted to 7.0 while that for gallium PPX was adjusted to 7.8. All solutions were filtered twice through 0.22 µm filter.

Example 12

In Vitro Effect of Gallium

Several mucoid and non-mucoid strains of *P. aeruginosa* were plated onto cetrimide agar plates to grow over night. The cultures were picked from the plates and inoculated into 1% Trypticase Soy Broth (TSB). When the optical density (OD$_{590nm}$) read 0.4 (mid-exponential growth phase), the broth content was diluted into iron-starved BM-2 broth containing various concentrations of gallium nitrate. The sample was grown for 24 hours and then the OD$_{590nm}$ was measured. Minimum inhibitory concentration (MIC) was determined for gallium nitrate for the various species shown in Table 11. Values for Tobramycin and Aztreonam are given for comparison.

TABLE 11

| | Tobramycin MIC (µg/mL) | Aztreonam MIC (µg/mL) | Gallium MIC (µg/mL) |
|---|---|---|---|
| Mucoid Strain | | | |
| 96JC | 16 (R)* | 32 (R) | <1 |
| 47JS | 32 (R) | 16 (I) | <1 |
| 97JE | 256 (R) | 32 (R) | <1 |
| 41JQ | 256 (R) | 32 (R) | <32 |
| 20JR | 4 (S) | 8 (S) | <1 |
| 62LL | 1 (S) | 32 (R) | <1 |
| 35LK | 8 (I) | 1 (S) | <1 |
| Non-mucoid Strain | | | |
| 9HN | 128 (R) | 32 (R) | <2 |
| 39IV | 4 (S) | 32 (R) | <1 |
| 30IX | 16 (R) | 1 (S) | <1 |
| 46IV | 64 (R) | 32 (R) | <1 |
| 55HY | 128 (R) | 16 (I) | <1 |
| 30JS | 1 (S) | 4 (S) | <1 |
| 38LL | 16 (I) | 32 (R) | <1 |

*R (resistant); S (susceptible); I (intermediate)

Example 13

In Vitro Effect of Gallium Against *P. aeruginosa*

Several mucoid and non-mucoid strains of *P. aeruginosa* (obtained from Columbia University, Pediatric Infectious Diseases Division) were plated onto cetrimide agar plates to grow over night. The cultures were picked from the plates and inoculated into 1% Trypticase Soy Broth (TSB). When the optical density ($OD_{590nm}$) read 0.4 (mid-exponential growth phase), the broth content was diluted into iron-starved BM-2 broth containing various concentrations of gallium nitrate. *P. aeruginosa* was grown in the presence of gallium-containing compositions and the optical density ($OD_{590nm}$) was measured at various time points after exposure. In some cases, the same strains exposed to gallium-containing compositions were also tested with Aztreonam and Tobramycin at similar concentrations for comparison of efficacy.

Example 14

In Vitro Effect of Gallium Against *P. aeruginosa*

Figure 7:
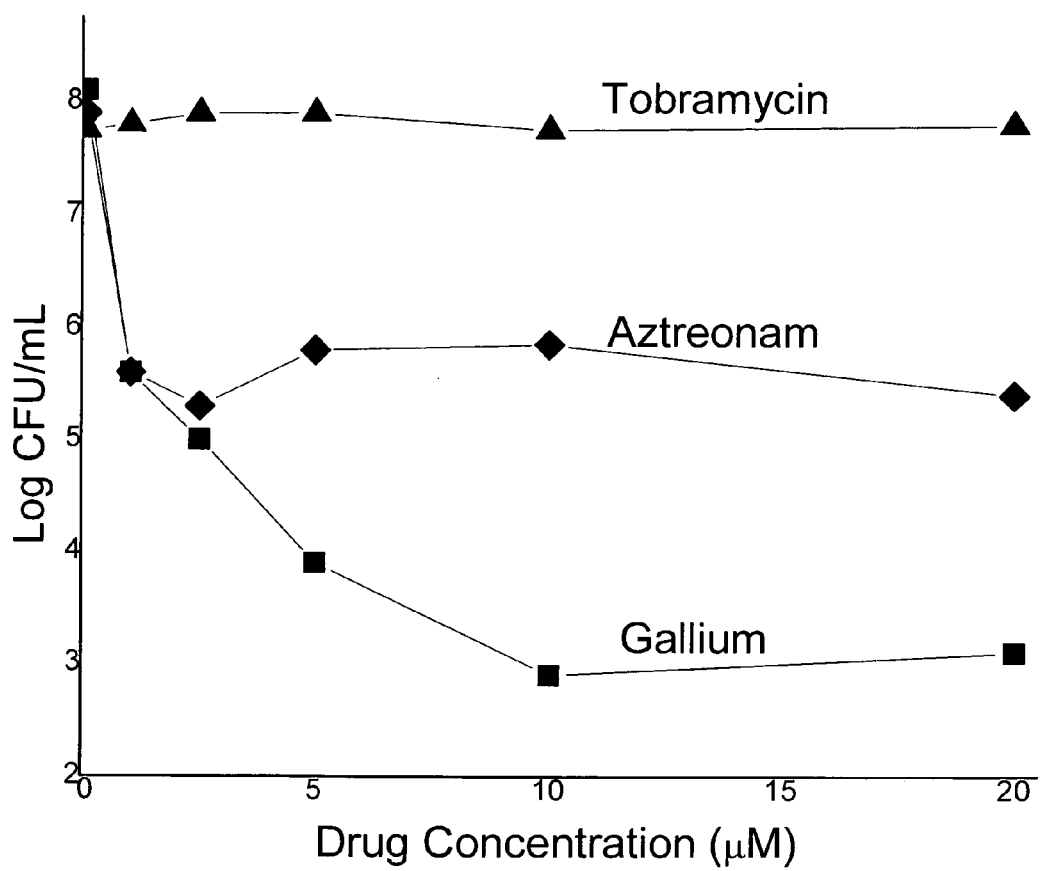
FIG. 7 shows the effect of gallium nitrate-citrate compositions on the growth of isolated non-mucoid strain of *P. aeruginosa*, 46IV. Gallium concentration ranged from 0 to 250 micromolar.

Isolated non-mucoid strain of *P. aeruginosa*, 46IV was plated onto cetrimide agar plates to grow over night. The cultures were picked from the plates and inoculated into 1% Trypticase Soy Broth (TSB). When the optical density ($OD_{590nm}$) read 0.4 (mid-exponential growth phase), the broth content was diluted into iron-starved BM-2 broth containing various concentrations of gallium nitrate-citrate compositions, ranging from 0 to 250 µM gallium at 1:1 gallium-to-citrate molar ratio. At various times after gallium exposure, samples were plated out on cetrimide agar plates to enumerate the remaining bacterial titer (FIG. 7).

Example 15

In Vitro Effect of Gallium Against *B. dolosa*

Figure 8:
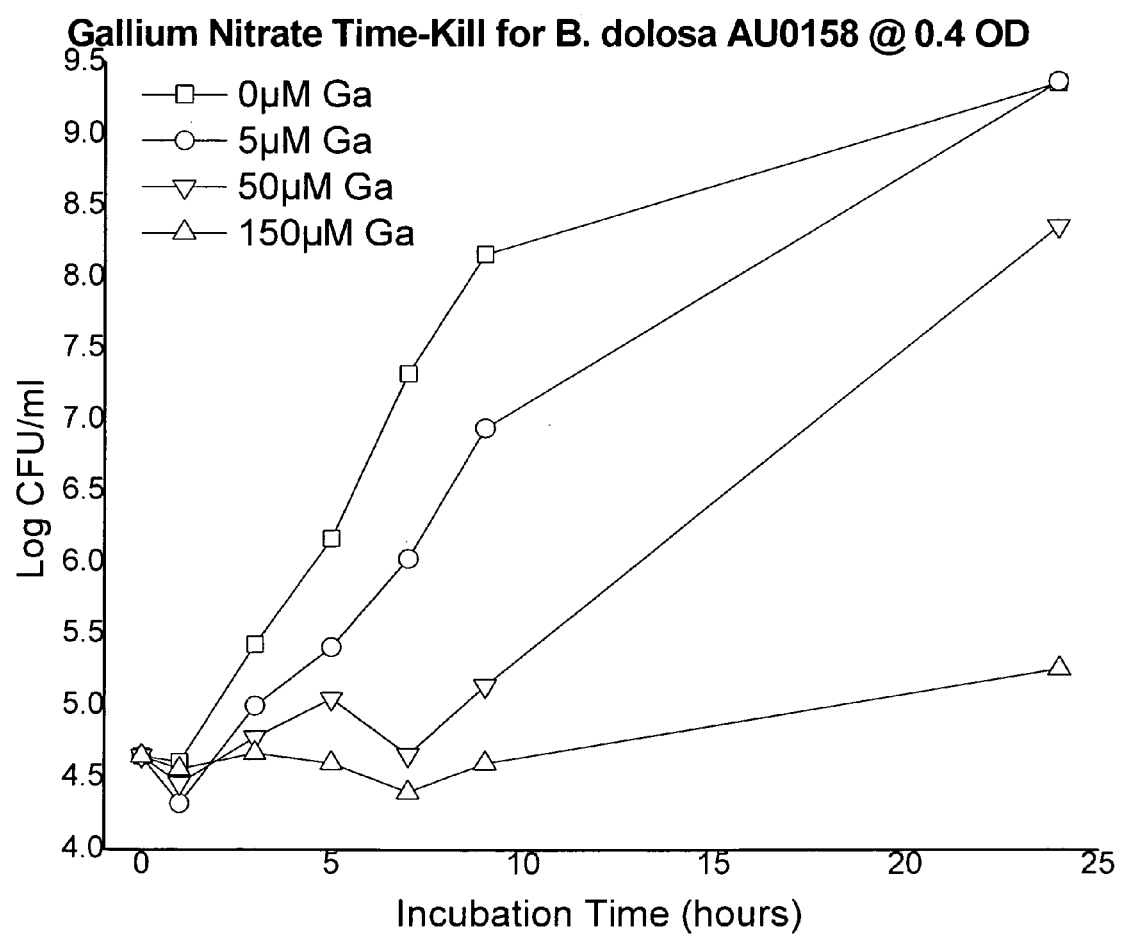
FIG. 8 shows the effect of gallium nitrate-citrate compositions on the growth of isolated strain of *B. dolosa*, AU0158. Gallium concentration ranged from 0 to 150 µM.

Isolated strain of *Burkholderia dolosa*, AU0158 obtained from Channing Laboratory, Department of Medicine, Brigham and Women's Hospital/Harvard Medical School, was plated onto cetrimide agar plates to grow over night. The cultures were picked from the plates and inoculated into 1% Trypticase Soy Broth (TSB). When the optical density ($OD_{590nm}$) read 0.4 (mid-exponential growth phase), the broth content was diluted into iron-starved BM-2 broth containing various concentrations of gallium nitrate-citrate compositions, ranging from 0 to 150 µM gallium at 1:1 gallium-to-citrate molar ratio. At various times after gallium exposure, samples were plated out on cetrimide agar plates to enumerate the remaining bacterial titer (FIG. 8).

Example 16

In Vitro Effect of Gallium Against *A. baumannii*

Figure 9:
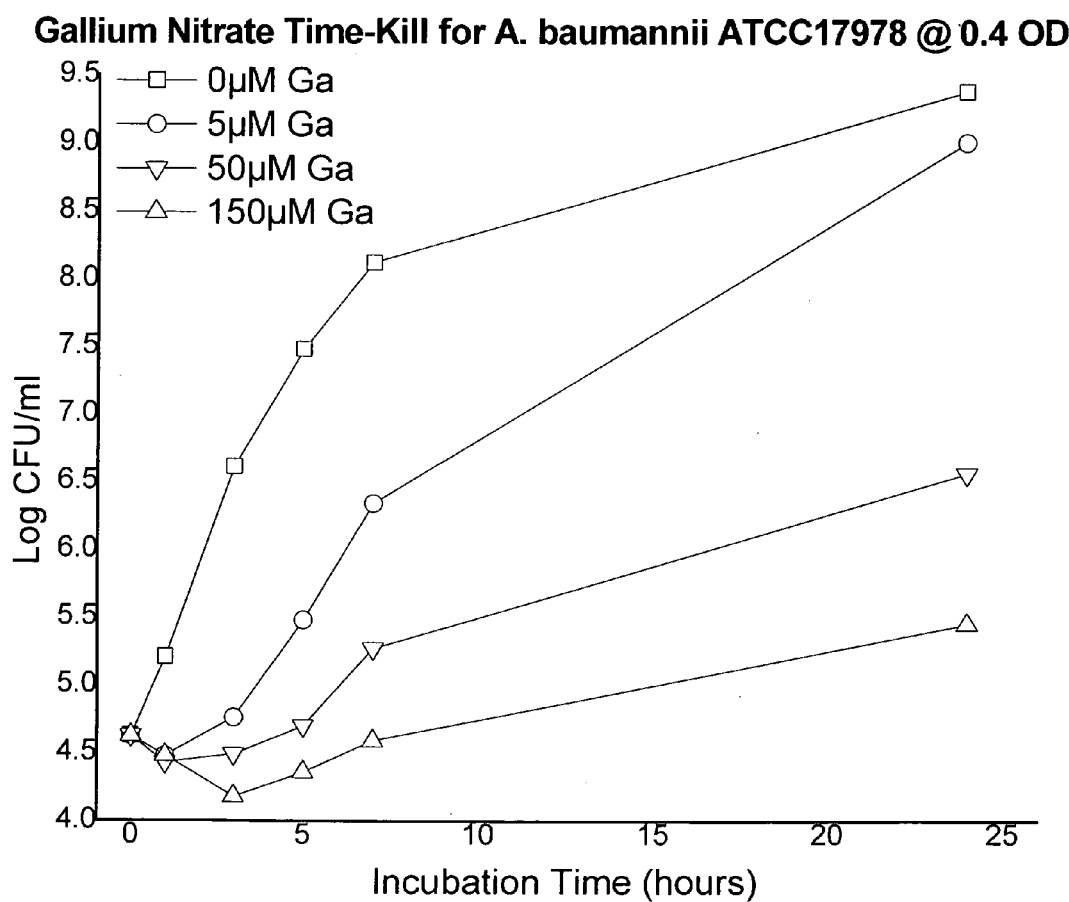
FIG. 9 shows the effect of gallium nitrate-citrate compositions on the growth of isolated strain of *A. baumannii*, ATCC 17978. Gallium concentration ranged from 0 to 150 micromolar.
Figure 10:
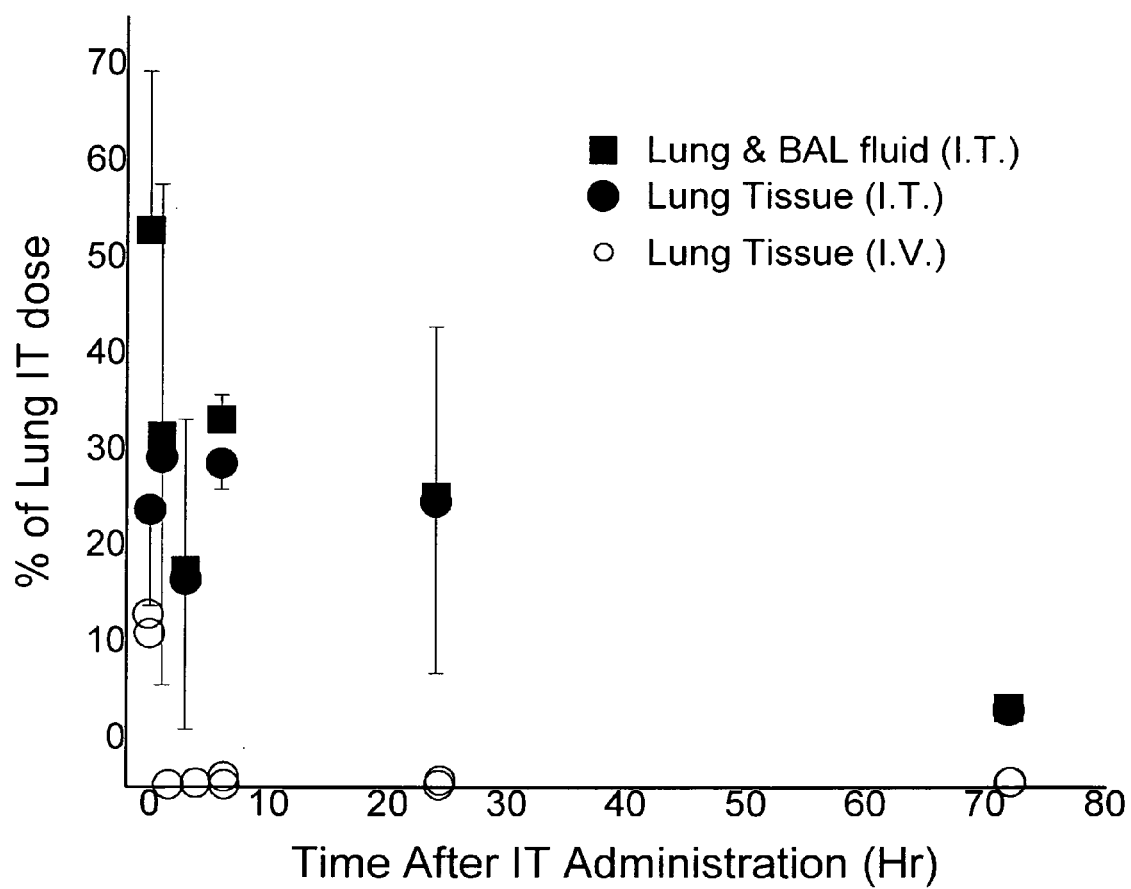
FIG. 10 shows the in vivo pharmacokinetics of gallium administered to adult Sprague-Dawley rats either intratracheally (i.t.) or intravenously (i.v.). The amount of gallium remaining in lung tissue and BAL (only for i.t. administered rats) is shown.

Isolated strain of *Acinetobacter baumannii*, ATCC 17978 obtained from Channing Laboratory, Department of Medicine, Brigham and Women's Hospital/Harvard Medical School, was plated onto cetrimide agar plates to grow over night. The cultures were picked from the plates and inoculated into 1% Trypticase Soy Broth (TSB). When the optical density ($OD_{590nm}$) read 0.4 (mid-exponential growth phase), the broth content was diluted into iron-starved BM-2 broth containing various concentrations of gallium nitrate, ranging from 0 to 150 µM gallium at 1:1 gallium-to-citrate molar ratio. At various times after gallium exposure, samples were plated out on cetrimide agar plates to enumerate the remaining bacterial titer (FIG. 9).

Example 17

In Vitro Effect of Gallium Against *B. anthracis*

*B. anthracis* 7702 cells were grown overnight in 1% Trypticase Soy Broth (TSB) at 37° C. with shaking to an optical density ($OD_{600nm}$) of ~5. The cells were then diluted to an $OD_{600nm}$ of 0.05 in TSB and grown for approximately 3 hours. Once the $OD_{600nm}$ had reached 0.75, the cells were pelleted, washed with PBS, and resuspended in TSB at a concentration of ~$10^5$ cells/mL. 10 mL of the diluted culture was mixed with freshly prepared gallium solution containing various concentrations of gallium nitrate, ranging from 0 to 1710 µM gallium at 1:1 gallium-to-citrate molar ratio. Cells were incubated overnight at 37° C. with shaking, and $OD_{600nm}$ measurements were conducted after approximately 20 hours of growth. The results are shown below (Table 12).

TABLE 12

| Gallium concentration (µM) | $OD_{600\,nm}$ |
|---|---|
| 0 | 0.114 |
| 6.8 | 0.000 |
| 23.3 | 0.000 |
| 27.1 | 0.001 |
| 88.9 | 0.003 |
| 614.8 | 0.000 |
| 1709.9 | 0.000 |

Example 18

In vivo Pharmacokinetics of Lung Administered Gallium. The residence time of aerosol formulations of gallium was tested in adult Sprague-Dawley rats by direct intratracheal (i.t.) delivery. A comparable formulation was delivered intravenously as control. Formulated gallium solution delivered i.t. exhibited significantly longer residence time in the lung than that delivered by the i.v. route (FIG. 10).

Example 19

Table 13 discloses the molar ratios of some of the formulations of the present invention. These formulations are non-limiting. Formulations 45, 49, and 50 contain no gallium. Formulations 44 and 48 contain gallium in a protoporphyrin salt (higher molecular weight than nitrate), thus the skewed ratio of mannitol and citrate to gallium for those compositions.

TABLE 13

| Molar ratios of components of gallium formulations | | | | | | | | |
|---|---|---|---|---|---|---|---|---|
| # | Ga | Citrate | Mannitol | Leu | Leu3 | D-leu | iso-leu | EtOH % (v/v) |
| 1 | 1.0 | 1.0 | | | | | | |
| 2 | 1.0 | 0.7 | 0.5 | | | | | |
| 3 | 1.0 | 0.7 | 0.6 | | 0.1 | | | |
| 4 | 1.0 | 0.7 | 0.6 | 1.0 | | | | |
| 5 | 1.0 | 0.7 | 0.6 | 2.2 | | | | |
| 6 | 1.0 | 0.7 | 0.6 | 0.5 | | | | |

TABLE 13-continued

Molar ratios of components of gallium formulations

|  | # | Ga | Citrate | Mannitol | Leu | Leu3 | D-leu | iso-leu | EtOH % (v/v) |
|---|---|---|---|---|---|---|---|---|---|
|  | 7 | 1.0 | 0.7 |  | 2.2 |  |  |  |  |
|  | 8 | 1.0 |  | 0.6 | 2.2 |  |  |  |  |
|  | 9 | 1.0 |  | 0.6 | 0.5 |  |  |  |  |
|  | 10 | 1.0 |  | 1.4 |  |  |  |  |  |
|  | 11 | 1.0 | 2.7 | 2.1 | 8.8 |  |  |  |  |
|  | 12 | 1.0 | 2.7 | 2.1 | 2.4 |  |  |  |  |
|  | 13 | 1.0 | 0.7 | 0.6 |  | 0.2 |  |  |  |
|  | 14 | 1.0 | 2.7 | 2.1 |  | 0.8 |  |  |  |
|  | 15 | 1.0 |  |  | 2.2 |  |  |  |  |
|  | 16 | 1.0 |  |  | 0.5 |  |  |  |  |
|  | 17 | 1.0 |  |  | 9.3 |  |  |  |  |
|  | 18 | 1.0 | 0.7 |  | 0.5 |  |  |  |  |
|  | 19 | 1.0 | 0.7 | 0.6 | 0.3 |  |  |  |  |
|  | 20 | 1.0 | 0.7 | 0.6 | 0.1 |  |  |  |  |
|  | 21 | 1.0 | 0.7 |  | 0.5 |  |  |  |  |
|  | 22 | 1.0 | 1.0 | 0.6 | 0.5 |  |  |  |  |
|  | 23 | 1.0 | 1.0 |  | 0.5 |  |  |  |  |
|  | 24 | 1.0 |  |  | 0.5 |  |  |  |  |
|  | 25 | 1.0 | 2.7 | 2.1 | 2.4 |  |  |  |  |
|  | 26 | 1.0 | 0.7 |  | 0.5 |  |  |  |  |
|  | 27 | 1.0 | 1.0 | 0.6 |  |  |  | 0.5 |  |
|  | 28 | 1.0 |  |  |  |  | 0.5 |  |  |
|  | 29 | 1.0 | 1.0 | 0.6 |  |  | 0.5 |  |  |
|  | 30 | 1.0 | 1.0 |  |  |  |  |  | 30 |
|  | 31 | 1.0 | 1.0 |  |  |  |  |  | 50 |
|  | 32 | 1.0 | 1.0 |  | 0.5 |  |  |  | 10 |
|  | 33 | 1.0 | 1.0 |  | 0.5 |  |  |  | 30 |
|  | 34 | 1.0 | 1.0 |  | 0.5 |  |  |  | 50 |
|  | 35 | 1.0 | 1.0 | 0.02 | 0.6 |  |  |  | 10 |
|  | 36 | 1.0 | 1.0 | 0.02 | 0.6 |  |  |  | 30 |
|  | 37 | 1.0 | 1.0 | 0.02 | 0.6 |  |  |  | 50 |
|  | 38 | 1.0 | 1.0 | 0.1 | 0.6 |  |  |  | 10 |
|  | 39 | 1.0 | 1.0 | 0.1 | 0.6 |  |  |  | 30 |
|  | 40 | 1.0 | 1.0 | 0.1 | 0.6 |  |  |  | 50 |
|  | 41 | 1.0 | 1.0 | 0.6 | 0.6 |  |  |  | 10 |
|  | 42 | 1.0 | 1.0 | 0.6 | 0.6 |  |  |  | 50 |
|  | 43 | 1.0 | 1.0 | 1.9 |  |  |  |  |  |
| GaPPX | 44 | 1.0 | 36.1 | 69.2 |  |  |  |  |  |
| no gallium | 45 |  |  |  |  |  |  |  |  |
|  | 46 | 1.0 | 1.0 | 0.1 |  |  |  |  |  |
|  | 47 | 1.0 | 1.0 | 0.1 | 0.1 |  |  |  |  |
|  | 48 | 1.0 | 36.1 | 69.2 |  |  |  |  |  |
| no gallium | 49 |  |  |  |  |  |  |  |  |
| no gallium | 50 |  |  |  |  |  |  |  |  |

Example 20

Effect of Citrate-to-Gallium Ratios on Solubility. The following concerns the preparation of various embodiments of the formulation of the present invention, to be used for aerosol administration. In order to determine the solubility of gallium-citrate mixtures, the gallium concentration, the citrate-to-gallium ratio, and solution pH were varied. 58.7 mM of gallium nitrate was mixed with appropriate amounts of sodium citrate to obtain the ratios shown in Table 14 below. When added, the sodium citrate was solid (crystalline or powdered) sodium citrate dihydrate. Mixing was by way of manual shaking in a test tube, and dissolving was facilitated by warming in a hot water bath, where the bath was held at about 60-80° C. The pH was adjusted to the values indicated (pH 3, 7, or 10) using NaOH or HCl. The solubility of the mixture was determined visually, i.e., by the lack of a precipitate. The term "precipitate," encompasses either that the gallium nitrate and sodium citrate never fully dissolved in solution, or that the gallium nitrate and sodium citrate were fully dissolved, but that a precipitate formed with when the mixture was allowed to reach room temperature. To adjust the pH, 10N NaOH was initially added with monitoring of the pH. As the pH approached the desired pH, 1N NaOH was added, instead of the 10N NaOH. While the time until assessment of precipitation is not critical, we waited about 48 hours until assessing precipitation, in order to ensure that the solution was stable for extended periods of time.

At the given gallium concentration, any citrate-to-gallium molar ratios greater or equal to 1-to-1 resulted in a soluble mixture for the solution pH ranges studied. In the absence of citrate, however, the gallium-citrate mixture was not soluble at neutral-to-alkaline conditions.

Table 14.

Effect of citrate-to-gallium mol ratio on the solubility of mixture at various pH, ranging from pH3 to 10. Gallium was present at 58.7 mM and appropriate amounts of sodium citrate, according to the molar ratio shown below, were added, followed by pH adjustment. The examples in the following two tables, relating to precipitation, demonstrate the effect of citrate-to-gallium molar ratio on the solubility of the mixture. Solubility was determined by whether the solids went into solution, or whether they precipitated during short-term storage, as judged visually. The example demonstrates that 2:1 citrate-to-gallium ratio result in the highest solubility, in a wide pH range (pH 3-10), thus allowing one to increase the gallium dose per given volume. In the event that there are solubility limitations (as may be the case at 1:1 ratio), then it may not be feasible to deliver a therapeutic dose of gallium in a practical amount of dose or time. The results from these two tables have application to use as an aerosol, and can also provide guidance for dry powder formulations.

TABLE 14

| Citrate/Gallium (mol ratio) | pH | Precipitate? |
|---|---|---|
| 0 | 3 | No |
| 0 | 7 | Yes |
| 0 | 10 | Yes |
| 1 | 3 | No |
| 1 | 7 | No |
| 1 | 10 | No |
| 2 | 3 | No |
| 2 | 7 | No |
| 2 | 10 | No |
| 3 | 3 | No |
| 3 | 7 | No |
| 3 | 10 | No |

Example 21

Effect of Citrate-to-Gallium Ratios on Solubility. In order to determine the solubility of gallium-citrate mixtures, the gallium concentration, the citrate-to-gallium ratio, and solution pH were varied. Gallium nitrate (234.6 mM) was mixed with appropriate amounts of sodium citrate to obtain the ratios shown in Table 15 below. The pH was adjusted to the values indicated (pH3, 7, or 10) using NaOH or HCl. The solubility of the mixture was determined visually, i.e., by the lack of precipitates. At the given gallium concentration, citrate-to-gallium molar ratio of 2 resulted in a soluble mixture for the solution pH ranges studied, whereas gallium solution containing no citrate was not soluble at any of the pH examined. At 1-to-1 molar ratio of citrate-to-gallium, precipitate was observed for solution prepared at pH10, while at 3-to-1 molar ratio, precipitate was observed at pH3.

Table 15.

Effect of citrate-to-gallium mol ratio on the solubility of mixture at various pH, ranging from pH3 to 10. Gallium was present at 234.6 mM and appropriate amounts of sodium citrate, according to the molar ratio shown below, were added, followed by pH adjustment. What is provided are formulations and solutions, where the molar ratio of citrate:gallium is about 1:1, about 1.2:1, about 1.3:1, about 1.4:1, about 1.5:1, about 1.6:1, about 1:7.1, about 1.8:1, about 1.9:1, about 2.0:1, or greater, where the formulation or solution has the following property. When tested at pH 10, according to the method disclosed herein, e.g., with gallium at 234.6 mM, there is no precipitate. Also, what is provided are formulations and solutions, where the molar ratio of citrate:gallium is at least 1:1, at least 1.2:1, at least 1.3:1, at least 1.4:1, at least 1.5:1, at least 1.6:1, at least 1:7.1, at least 1.8:1, at least 1.9:1, at least 2.0:1, or greater, where the formulation or solution has the following property. When tested at pH 10, according to the methods disclosed herein, e.g., with gallium at 234.6 mM, there is no precipitate.

In another aspect, the above tests can be performed where the concentration of gallium is 234.6 mM, 117.3 mM, 58.65 mM, 29.3 mM, or 14.6 mM, and so on, and formulations, solutions, and related methods, can be based on ratios of citrate:gallium that do not result in precipitation. In another aspect, an anion or complexing agent other than citrate can be used, and appropriate formulations, solutions, and methods of the present invention can be prepared.

TABLE 15

| Citrate/Gallium (mol ratio) | pH | Precipitate? |
|---|---|---|
| 0 | 3 | Yes |
| 0 | 7 | Yes |
| 0 | 10 | Yes |
| 1 | 3 | No |
| 1 | 7 | No |
| 1 | 10 | Yes |
| 1.5 | 3 | No |
| 1.5 | 7 | No |
| 1.5 | 10 | Yes |
| 2 | 3 | No |
| 2 | 7 | No |
| 2 | 10 | No |
| 3 | 3 | Yes |
| 3 | 7 | No |
| 3 | 10 | No |
| Gallium at 469.2 mM | | |
| 1 | 3 | Yes |
| 1 | 7 | No |
| 1 | 10 | (not tested because ppt was found with 234.6 mM) |
| 1.5 | 3 | No |
| 1.5 | 7 | No |
| 1.5 | 10 | (not tested because ppt was found with 234.6 mM) |
| 2 | 3 | No |
| 2 | 7 | No |
| 2 | 10 | Yes |

Example 22

Preparation of Dry Powder Gallium Using Spray Drying Method

Ga(NO$_3$)$_3$.9H$_2$O was dissolved to obtain 58.7 mM Ga(NO$_3$)$_3$. Sodium citrate dihydrate was added to the gallium solution at an amount corresponding to citrate-to-gallium molar ratios of 1:1, 2:1, and 3:1 (Table 16). To the solution, 30.5 mM L-leucine was added and the solution pH adjusted to 7. The mixture was spray-dried at T$_{in}$/T$_{out}$=80/60° C., q=0.5 mL/min, and P$_{atm}$=24 psi. The powder was collected under controlled temperature and humidity of 30° C. and <5% RH, respectively. 50 mg of the powder was encapsulated inside of a type 2 capsule and tested for particle size distribution using an Anderson cascade impactor (ACI) fitted with Turbospin® under a flow rate of 28 L/min. FPD$_{<3.3\mu m}$, FPD$_{<4.7\mu m}$, and MMAD were determined and are shown in the table below (Table 16).

Table 16.

Compositions comprised of 58.7 mM gallium at various citrate-to-gallium molar ratios, ranging from 1 to 3, and L-leucine at 30.5 mM. The aerosol properties, as characterized by ACI, are also given.

TABLE 16

| Formulation # | Citrate/Gallium (molar ratio) | Gallium (mM) | L-leucine (mM) | FPD$_{<3.3 \mu m}$ (%) | FPD$_{<4.7 \mu m}$ (%) | MMAD (μm) |
|---|---|---|---|---|---|---|
| 51 | 1 | 58.7 | 30.5 | 0.530 | 0.759 | 3.13 ± 0.06 |
| 52 | 2 | 58.7 | 30.5 | 0.403 | 0.613 | 3.87 ± 0.06 |
| 53 | 3 | 58.7 | 30.5 | 0.465 | 0.675 | 3.49 ± 0.11 |

Example 23

Preparation of Dry Powder Gallium Using Spray Drying Method

Ga(NO$_3$)$_3$·9H$_2$O was dissolved to obtain 58.7 mM Ga(NO$_3$)$_3$. Sodium citrate dihydrate was added to the gallium solution at an amount corresponding to citrate-to-gallium molar ratios of 2:1 (Table 17). Several amino acids, at a concentration corresponding to 1.2% (w/v), were added and the solution pH adjusted to 7. The mixture was spray-dried at T$_{in}$/T$_{out}$=80/60° C., q=0.5 mL/min, and P$_{atm}$=24 psi. The powder was collected under controlled temperature and humidity of 30° C. and <5% RH, respectively. 50 mg of the powder was encapsulated inside of a type 2 capsule and tested for particle size distribution using an Anderson cascade impactor (ACI) fitted with Turbospin® under a flow rate of 28 L/min. FPD$_{<3.3 \mu m}$, FPD$_{<4.7 \mu m}$, and MMAD were determined and are shown in the table below (Table 18).

Table 17.

Compositions comprised of 58.7 mM gallium at citrate-to-gallium molar ratio of 2 and an amino acid present at 1.2% (w/v). The amino acids examined included L-leucine, valine, histidine, and lysine.

TABLE 17

| Formulation # | Citrate/Gallium (molar ratio) | Gallium (mM) | Leucine (mM) | Valine (mM) | Histidine (mM) | Lysine (mM) |
|---|---|---|---|---|---|---|
| 54 | 2 | 58.7 | 91.6 | | | |
| 55 | 2 | 58.7 | | 102.4 | | |
| 56 | 2 | 58.7 | | | 77.3 | |
| 57 | 2 | 58.7 | | | | 82.1 |

Table 18.

The aerosol properties, as characterized by ACI, for the formulations described in Table 17.

TABLE 18

| Formulation # | FPD$_{<3.3 \mu m}$ (%) | FPD$_{<4.7 \mu m}$ (%) | MMAD (μm) |
|---|---|---|---|
| 54 | 64.1 ± 2.0 | 84.3 ± 2.0 | 2.67 ± 0.05 |
| 55 | 37.4 ± 3.2 | 62.8 ± 3.0 | 4.06 ± 0.23 |
| 56 | 33.9 ± 3.5 | 54.5 ± 3.0 | 4.61 ± 0.28 |
| 57 | 32.1 ± 1.6 | 51.6 ± 1.5 | 4.84 ± 0.16 |

Table 19 provides control values for particle size (MMAD), where the control particles were prepared without any amino acids.

TABLE 19

| | Formulation #1 | Formulation #2 | Formulation #3 |
|---|---|---|---|
| Citrate:Gallium | 0:1 | 1:1 | 2:1 |
| Weight (% gallium) | 27.26% | 13.57% | 9.03% |
| Excipient | none | none | none |
| Average MMAD | >9 | >9 | 8.05 +/− 1.04 |
| % MC | 9.21 | 8.13 +/− 0.06 | 7.35 +/− 0.34 |
| % Deposited | 7.90% | 22.35% +/− 7.71 | 26.65% +/− 1.34 |
| % Yield | 48.80% | 68.20% | 74.95% |
| FPD < 3 micrometers | 0.187 | 0.009 +/− 0.013 | 0.122 +/− 0.018 |
| FPD < 5 micrometers | 0.321 | 0.026 +/− 0.026 | 0.298 +/− 0.032 |

% MC means percent Moisture Content. In a preferred embodiment, the moisture content is minimal. Generally, with minimal moisture, the powder will aggregate minimally, for example, during storage.

Many modifications and variations of this invention, as will be apparent to one of ordinary skill in the art, can be made to adapt to a particular situation, material, composition of matter, or process, to preserve the objective, spirit, and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of the equivalents to which such claims are entitled; and the invention is not to be limited by the specific embodiments that have been presented herein by way of example.

What is claimed is:

1. A method for treating an infection comprising administering a pharmaceutical formulation to a subject having the infection, wherein the pharmaceutical formulation comprises a solution, or a dry powder derived from said solution, of an anti-microbially effective concentration of gallium (III) and citrate, wherein the molar ratio of citrate to gallium is 2:1.

2. The method of claim 1, wherein the infection comprises a pulmonary infection.

3. The method of claim 1, wherein the infection comprises:
   a. A gram-negative bacterium that is *Escherichia coli, Klebsiella pneumoniae, Klebsiella oxytoca, Pseudomonas aeruginosa, Haemophilus influenzae, Proteus mirabilis, Enterobacter* species, *Serratia marcescens, Burkholderia cepacia, Acinetobacter baumannii, Stenotrophomonas maltophilia, Alcaligenes xylosoxidans*, multidrug resistant *Pseudomonas aeruginosa*, or *Mycobacterium tuberculosis*, or
   b. A gram-positive bacterium that is *Staphylococcus aureus, Rhodococcus equi, Staphylococcus aureus*, methycillin resistant *Staphylococcus aureus* (MRSA), *Actinobacteria, Lactobacillales, Actinomycies*, or *Clostridium*.

4. The method of claim 1, wherein the subject has cystic fibrosis, bronchiectasis, chronic obstructive pulmonary diseases (COPD), or is a subject on a ventilator.

5. The method of claim 1, wherein adding a volume of the pharmaceutical formulation in a bolus to a ten fold greater volume of a biological fluid that is human plasma or an extracellular lung fluid, does not result in turbidity, where turbidity is assessed after adding the solution to the biological fluid.

6. The method of claim 1, wherein the molar ratio of nitrate:gallium is lower than 0.1:1.

7. The method of claim 1, wherein the solution is an aerosol.

8. The method of claim 1, wherein the formulation comprises a complexing agent selected from mannitol, maltolate, protoporphyrin IX or its derivative, siderophores of the catecholate, hydroxamate, and hydroxycarboxylate groups, bacterial hemophores, an iron chelator, or a mixture thereof.

9. The method of claim 1, wherein the formulation is a dry powder.

10. The method of claim 1, wherein the formulation further comprises a pharmaceutically acceptable excipient selected from:
   a) a polyol that is sucrose, trehalose, glucose, raffinose, sorbose, melezitose, glycerol, fructose, mannose, maltose, lactose, arabinose, xylose, ribose, rhamnose, galactose, glycose, mannitol, xylitol, erythritol, threitol, dextrose, fucose, polyaspartic acid, inositol hexaphosphate (phytic acid), sialic acid, N-acetylneuraminic acid-lactose, or sorbitol;
   b) an amino acid that is leucine, valine, isoleucine, tryptophan, alanine, methionine, phenylalanine, tyrosine, histidine, proline, their derivatives, and a mixture thereof;
   c) a tri-peptide comprised of two leucines and an amino acid, selected from leucine, valine, isoleucine, tryptophan, alanine, methionine, phenylalanine, tyrosine, histidine, and proline;
   d) a protein that is transferrin, lactoferrin, human serum albumin, or recombinant human serum albumin;
   e) an organic acid salt that is tartaric acid or tartrate, or lactic acid or lactate;
   f) a surfactant block co-polymers of polyethylene, polypropylene glycol, polyethylene glycol sorbitan monolaurate, or polyoxyethylenesorbitan monooleate;
   g) a polysaccharide that is alginic acid, alginates, heparin, heparin sulfates, hyaluronic acid, hyaluronates, chitosan, chitin, starch, starch derivatives, carboxymethyl starch, hydroxyethyl starch (HES), or dextran; or
   h) a polymer that is polyvinyl pyrrolidone (PVP), gelatin, collagen, chrondroitin sulfate, or polyvinyl alcohol (PVA).

11. The method of claim 1, wherein the powder has a pharmaceutically acceptable mass median aerodynamic diameter (MMAD), wherein the mean particle size is lower than 10 micrometers.

12. The method of claim 1, wherein the formulation comprises one or more of mannitol, leucine, or trileucine, and where the mean particle size is 10 micrometers or less.

13. The method of claim 1, wherein the formulation comprises leucine, trileucine,